United States Patent
Schouenborg

(10) Patent No.: US 11,583,233 B2
(45) Date of Patent: Feb. 21, 2023

(54) MEDICAL DEVICE COMPRISING AN ELECTRODE AND A LIGHT SOURCE

(71) Applicant: NEURONANO AB, Karlshamn (SE)

(72) Inventor: Jens Schouenborg, Lund (SE)

(73) Assignee: NEURONANO AB

( * ) Notice: Subject to any disclaimer, the term of this patent is extended or adjusted under 35 U.S.C. 154(b) by 511 days.

(21) Appl. No.: 15/106,688

(22) PCT Filed: Dec. 18, 2014

(86) PCT No.: PCT/SE2014/000152
§ 371 (c)(1),
(2) Date: Jun. 20, 2016

(87) PCT Pub. No.: WO2015/094076
PCT Pub. Date: Jun. 25, 2015

(65) Prior Publication Data
US 2017/0000419 A1 Jan. 5, 2017

(30) Foreign Application Priority Data

Dec. 20, 2013 (SE) .................................. 1300786-9

(51) Int. Cl.
| | |
|---|---|
| *A61B 5/00* | (2006.01) |
| *A61N 1/05* | (2006.01) |
| *A61N 5/06* | (2006.01) |
| *A61N 1/372* | (2006.01) |
| *A61B 17/00* | (2006.01) |
| *A61N 5/067* | (2006.01) |

(52) U.S. Cl.
CPC ............ *A61B 5/686* (2013.01); *A61B 5/0086* (2013.01); *A61N 1/0529* (2013.01);
(Continued)

(58) Field of Classification Search
CPC ......... A61B 5/00; A61B 5/686; A61B 5/0086; A61B 2017/00057; A61B 2560/063;
(Continued)

(56) References Cited

U.S. PATENT DOCUMENTS 8,386,006 B2 * 2/2013 Schouenborg ....... A61N 1/0551
600/373
2003/0216622 A1* 11/2003 Meron ............... A61B 1/00147
600/300
(Continued)

FOREIGN PATENT DOCUMENTS

| EP | 2 630 986 A2 | 8/2013 |
| SE | 1350409 A1 | 9/2014 |

(Continued)

OTHER PUBLICATIONS

International Search Report dated Apr. 29, 2015 issued in corresponding International patent application No. PCT/SE2014/000152.

*Primary Examiner* — Eun Hwa Kim
*Assistant Examiner* — Catherine Premraj
(74) *Attorney, Agent, or Firm* — Ostrolenk Faber LLP

(57) ABSTRACT

A device for insertion into soft tissue including a micro electrode, a micro light source; a stiffening element having a material dissolvable or degradable in aqueous body fluid or a material swellable in such fluid to form a transparent gel; a coat of a flexible non-conducting polymer material on the stiffening element; a base disposed at the rear end of the device. The flexible coat has a distal opening allowing light emitted from the light source to leave the device upon said collapse or dissolution or swelling. Also disclosed is a therapeutic or diagnostic device formed in the tissue from the insertable device, uses thereof, and a method of disposing the insertable device in soft tissue.

35 Claims, 20 Drawing Sheets

(52) U.S. Cl.
CPC ...... *A61N 1/37205* (2013.01); *A61N 1/37211* (2013.01); *A61N 5/0601* (2013.01); *A61N 5/0622* (2013.01); *A61B 2017/00057* (2013.01); *A61B 2560/063* (2013.01); *A61B 2562/028* (2013.01); *A61N 5/067* (2021.08); *A61N 2005/063* (2013.01); *A61N 2005/0612* (2013.01); *A61N 2005/0651* (2013.01)

(58) Field of Classification Search
CPC ............ A61B 2562/028; A61N 1/0529; A61N 1/37205; A61N 1/37211; A61N 5/0601; A61N 5/0622; A61N 2005/0612; A61N 2005/063; A61N 2005/0651; A61N 2005/067
See application file for complete search history.

(56) References Cited

U.S. PATENT DOCUMENTS

| | | | |
|---|---|---|---|
| 2006/0229711 A1* | 10/2006 | Yan | A61F 2/02 623/1.38 |
| 2008/0275428 A1 | 11/2008 | Tegg et al. | |
| 2009/0259274 A1 | 10/2009 | Simon et al. | |
| 2009/0275799 A1* | 11/2009 | Saadat | A61B 1/0008 600/109 |
| 2011/0046148 A1 | 2/2011 | Himmelsbach et al. | |
| 2011/0288547 A1 | 11/2011 | Morgan et al. | |
| 2011/0313271 A1 | 12/2011 | Schulman | |
| 2012/0123318 A1* | 5/2012 | Ek | A61B 5/04001 604/20 |
| 2012/0209344 A1* | 8/2012 | Rossi | A61N 1/37205 607/22 |
| 2013/0237906 A1 | 9/2013 | Park et al. | |
| 2013/0253261 A1 | 9/2013 | Augarten | |
| 2014/0324143 A1* | 10/2014 | Robinson | A61N 1/05 607/116 |

FOREIGN PATENT DOCUMENTS

| | | |
|---|---|---|
| WO | WO 02/43623 A1 | 6/2002 |
| WO | WO 2013191612 A1 | 11/2008 |
| WO | WO 2009/075625 A1 | 6/2009 |
| WO | WO 2010/144016 | 12/2010 |
| WO | WO 2011/057137 A1 | 5/2011 |
| WO | WO 2012/170340 A2 | 12/2012 |
| WO | WO 2008/137851 A1 | 12/2013 |

\* cited by examiner

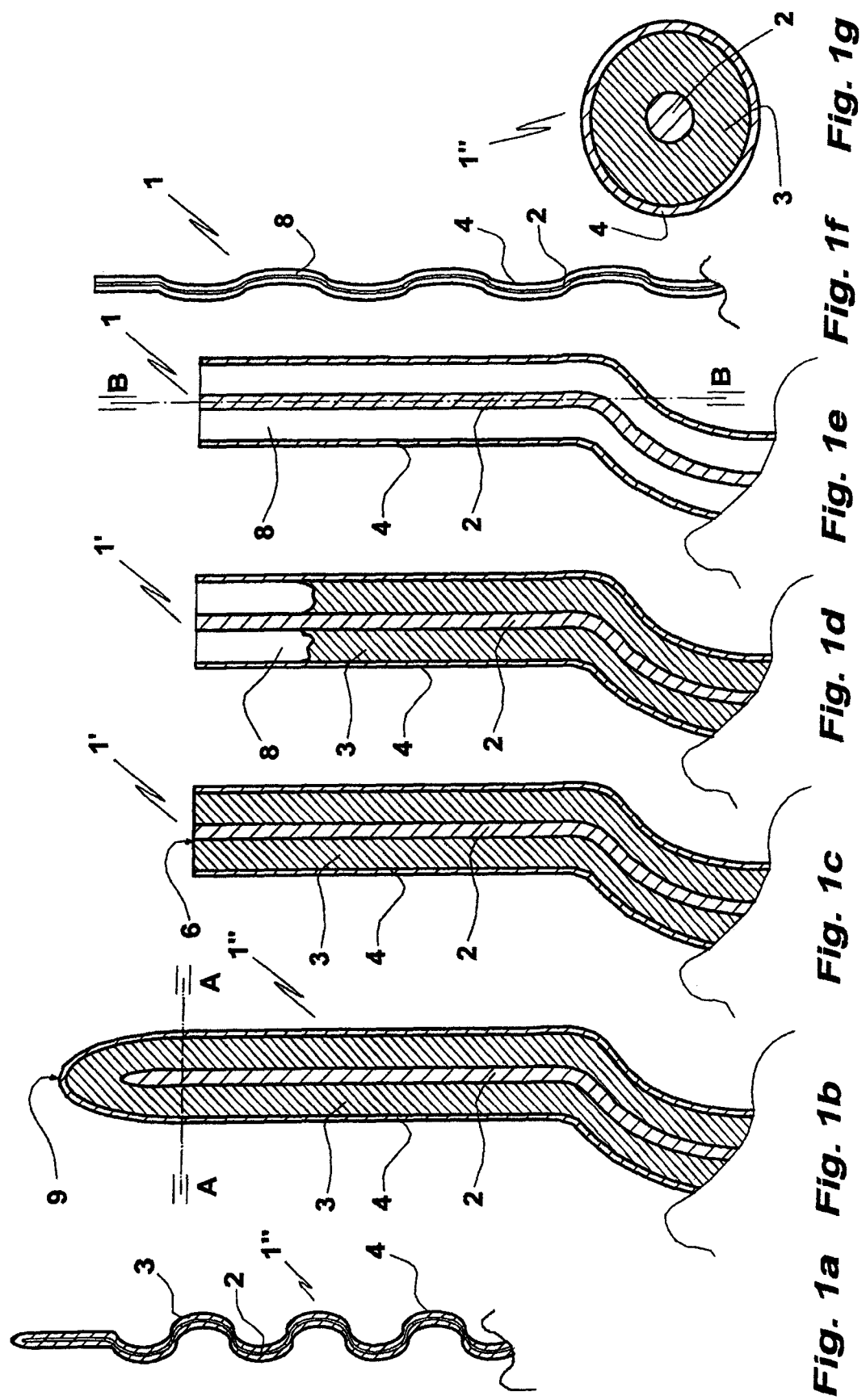

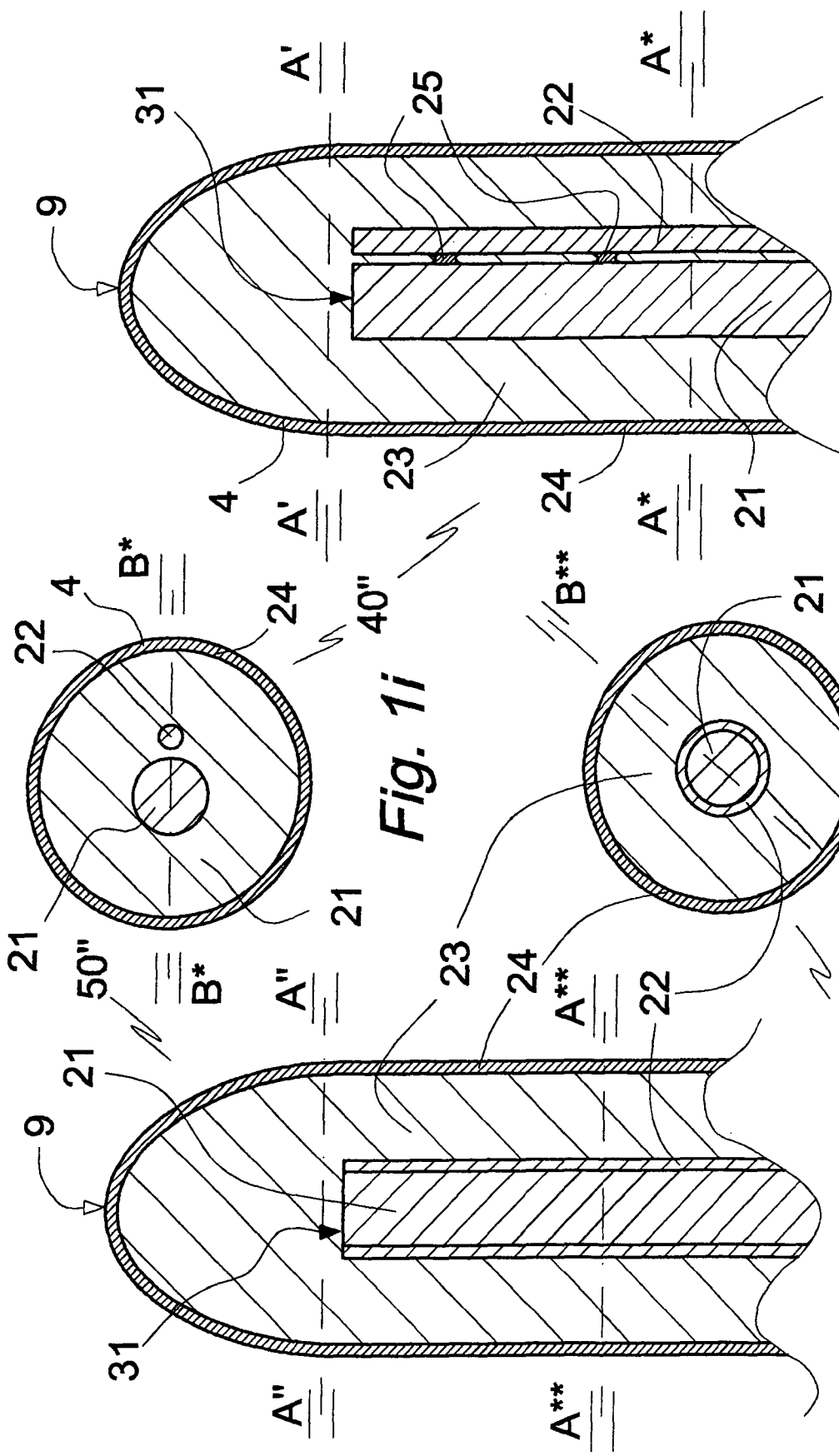

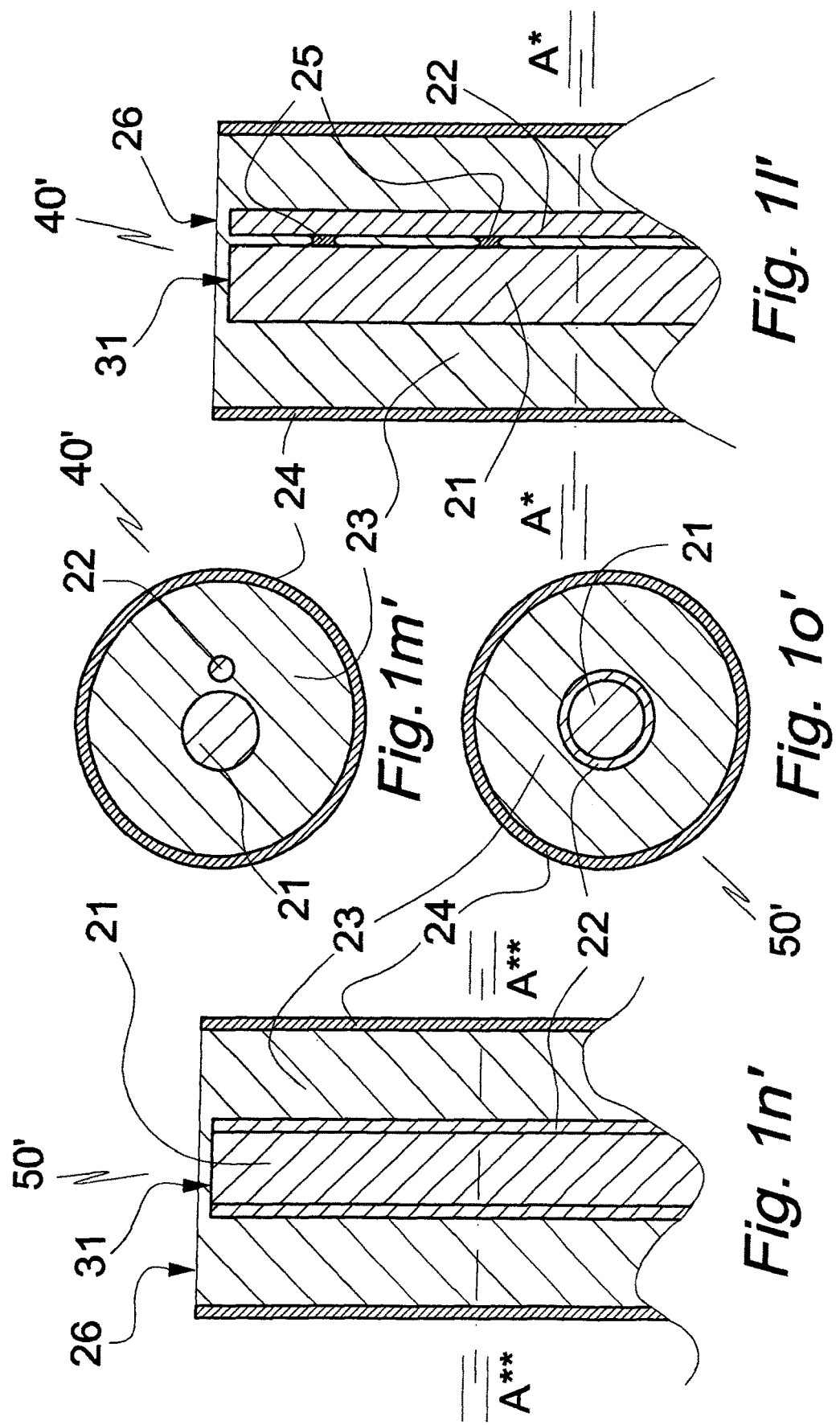

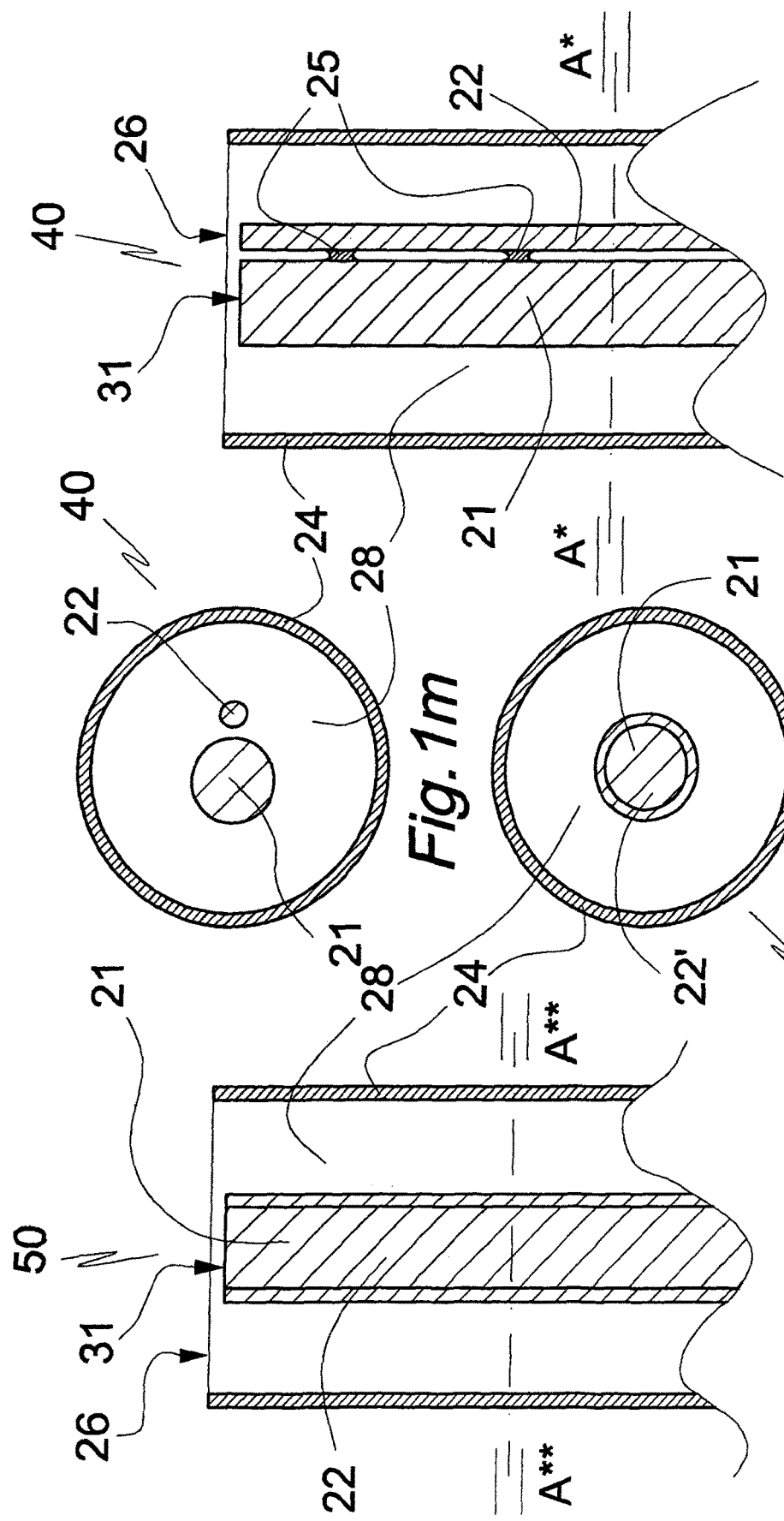

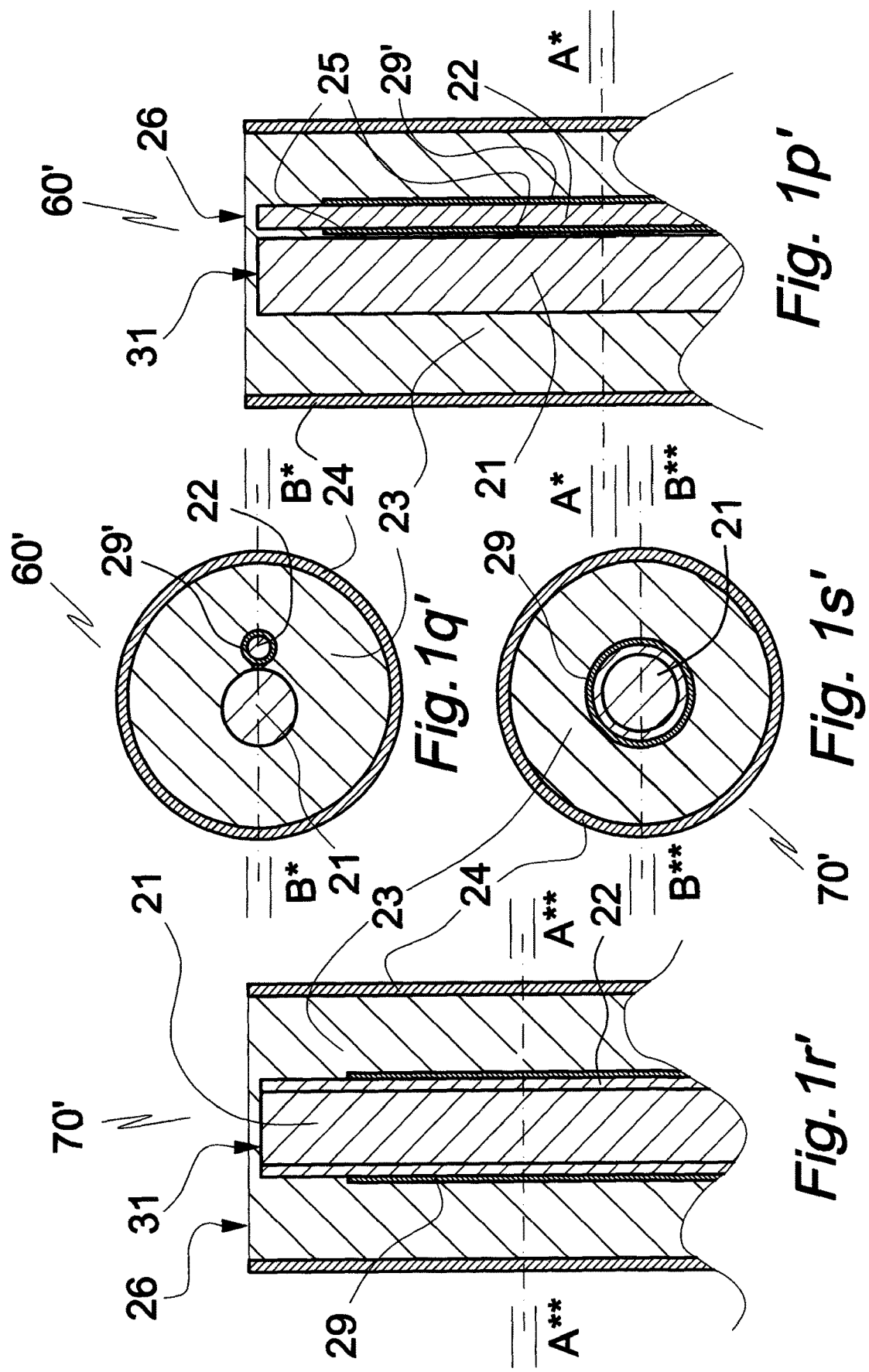

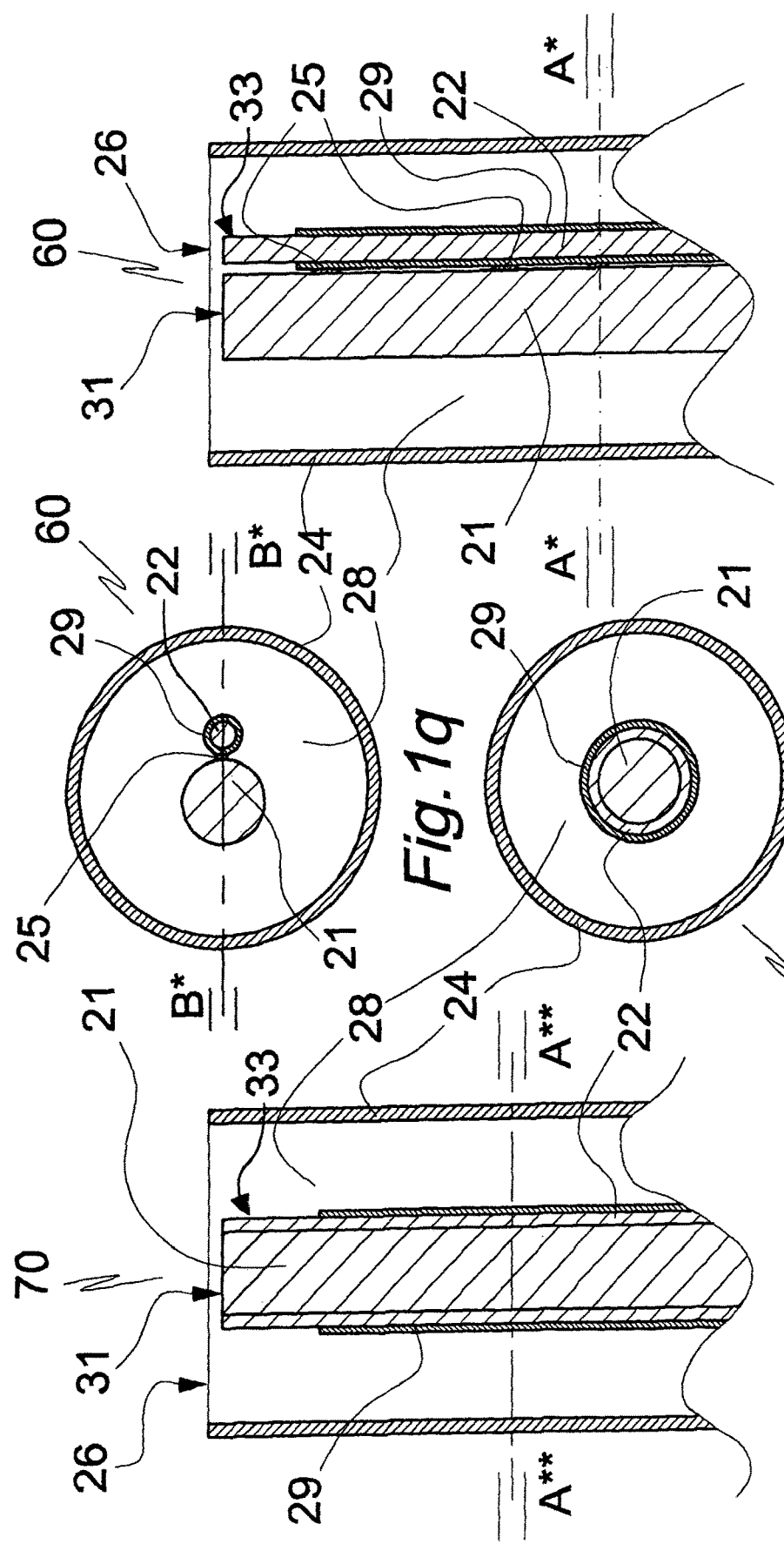

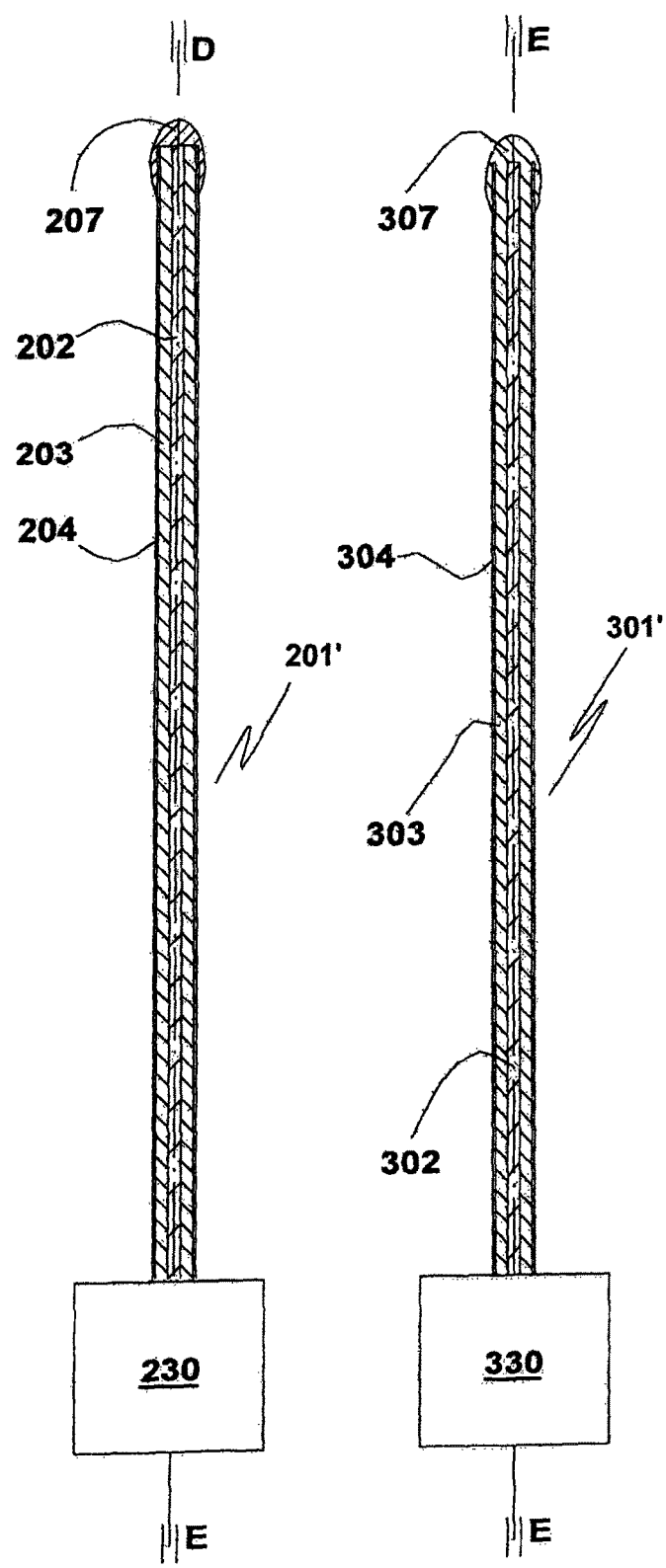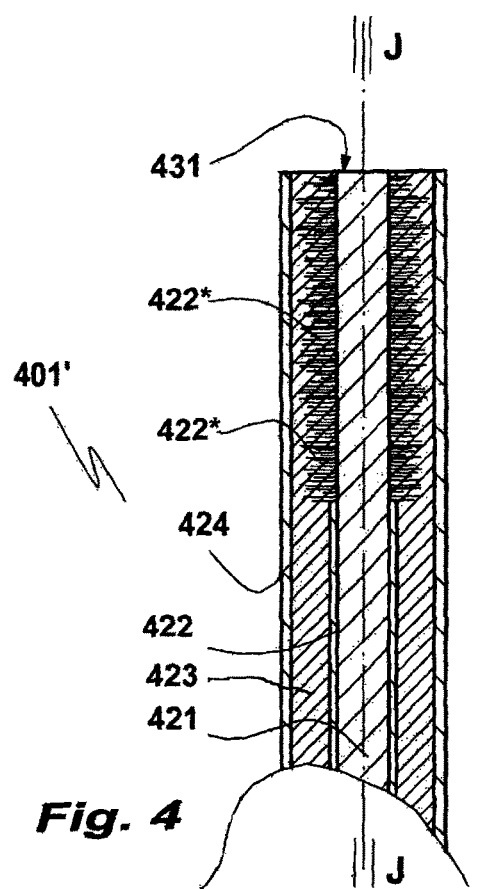

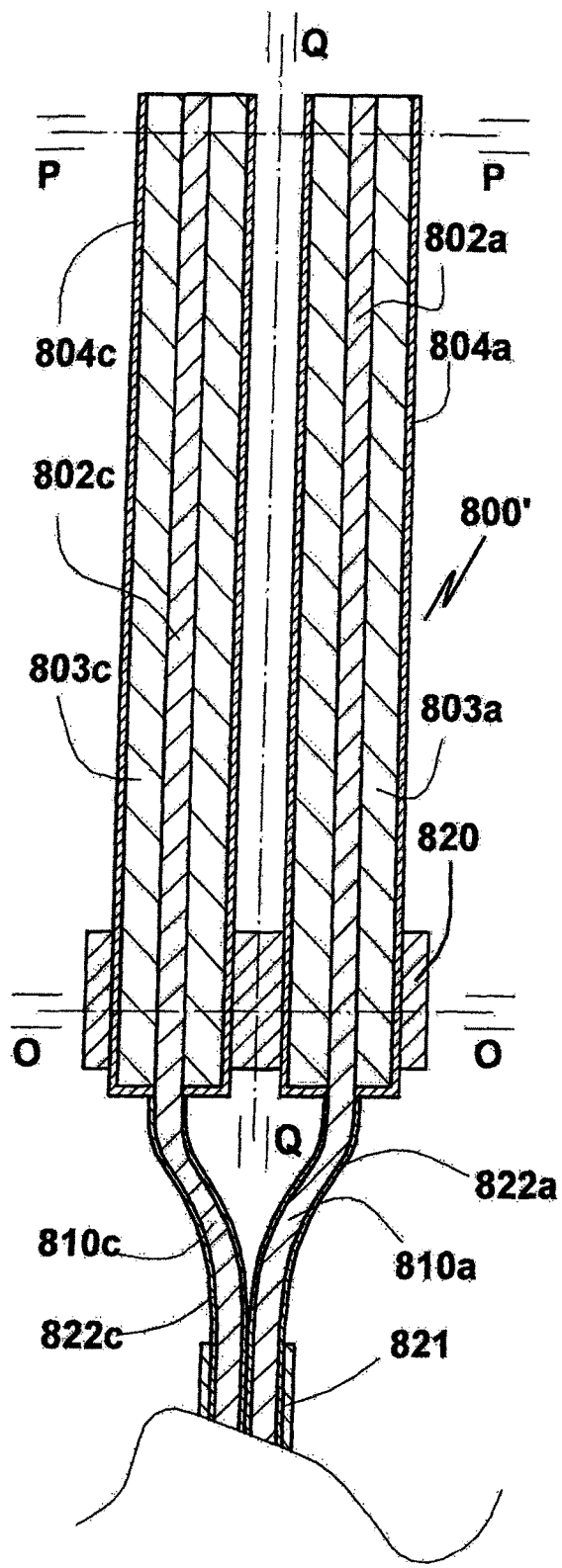
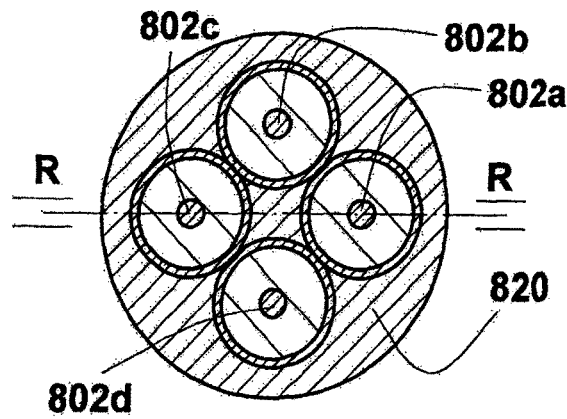
Fig. 9b
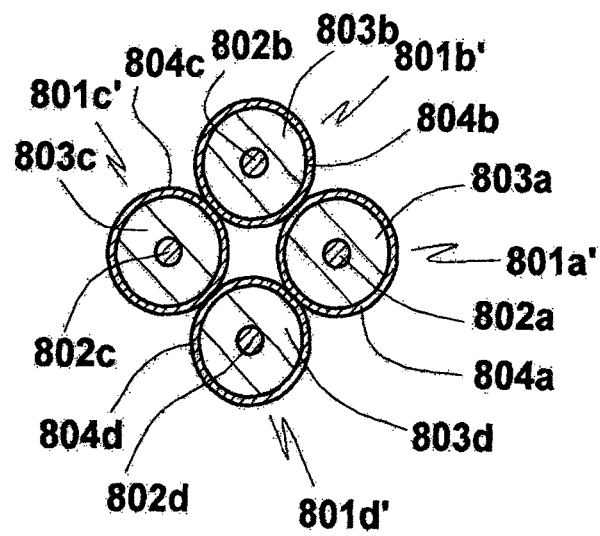
Fig. 9c
Fig. 9a

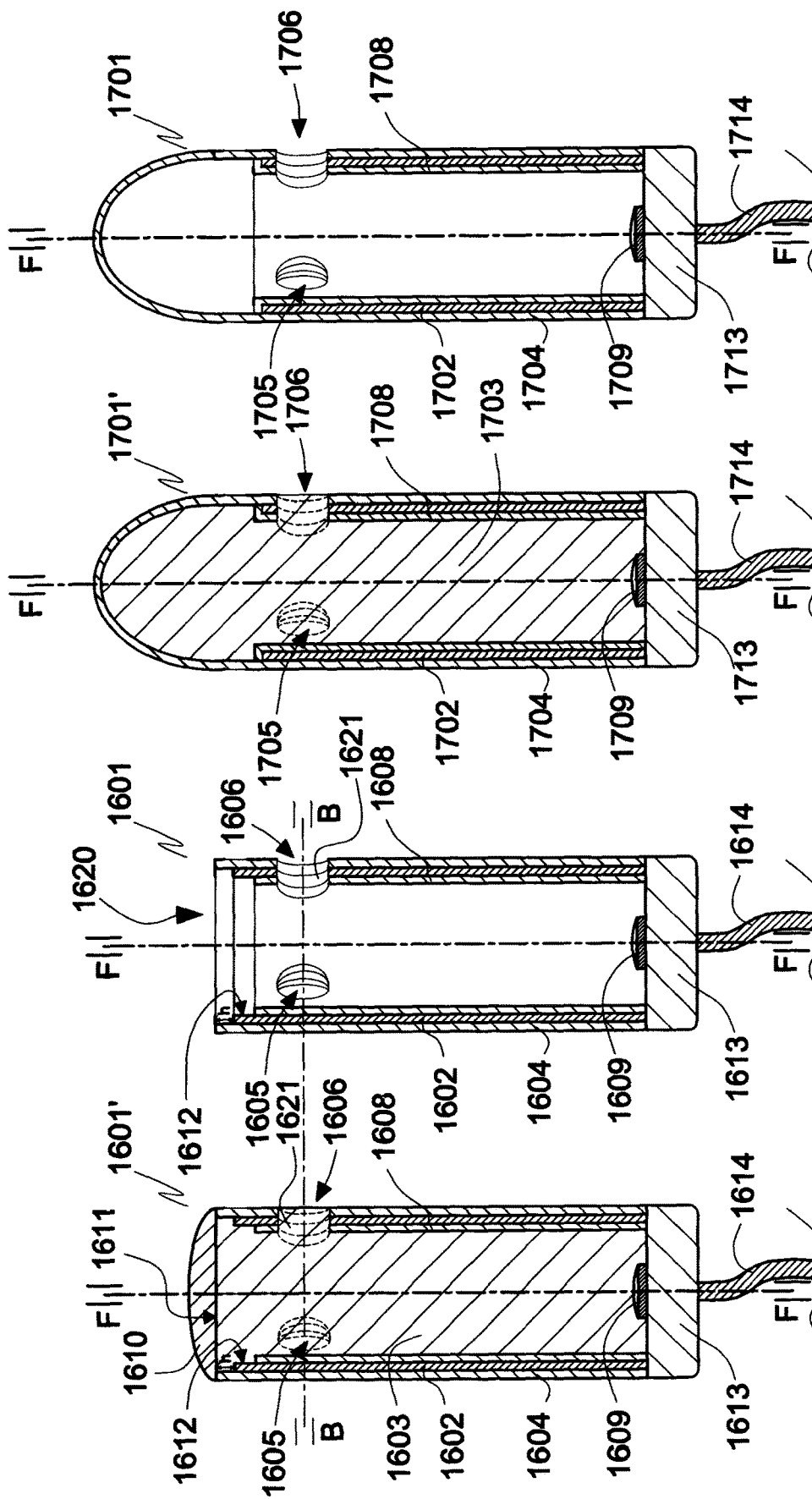

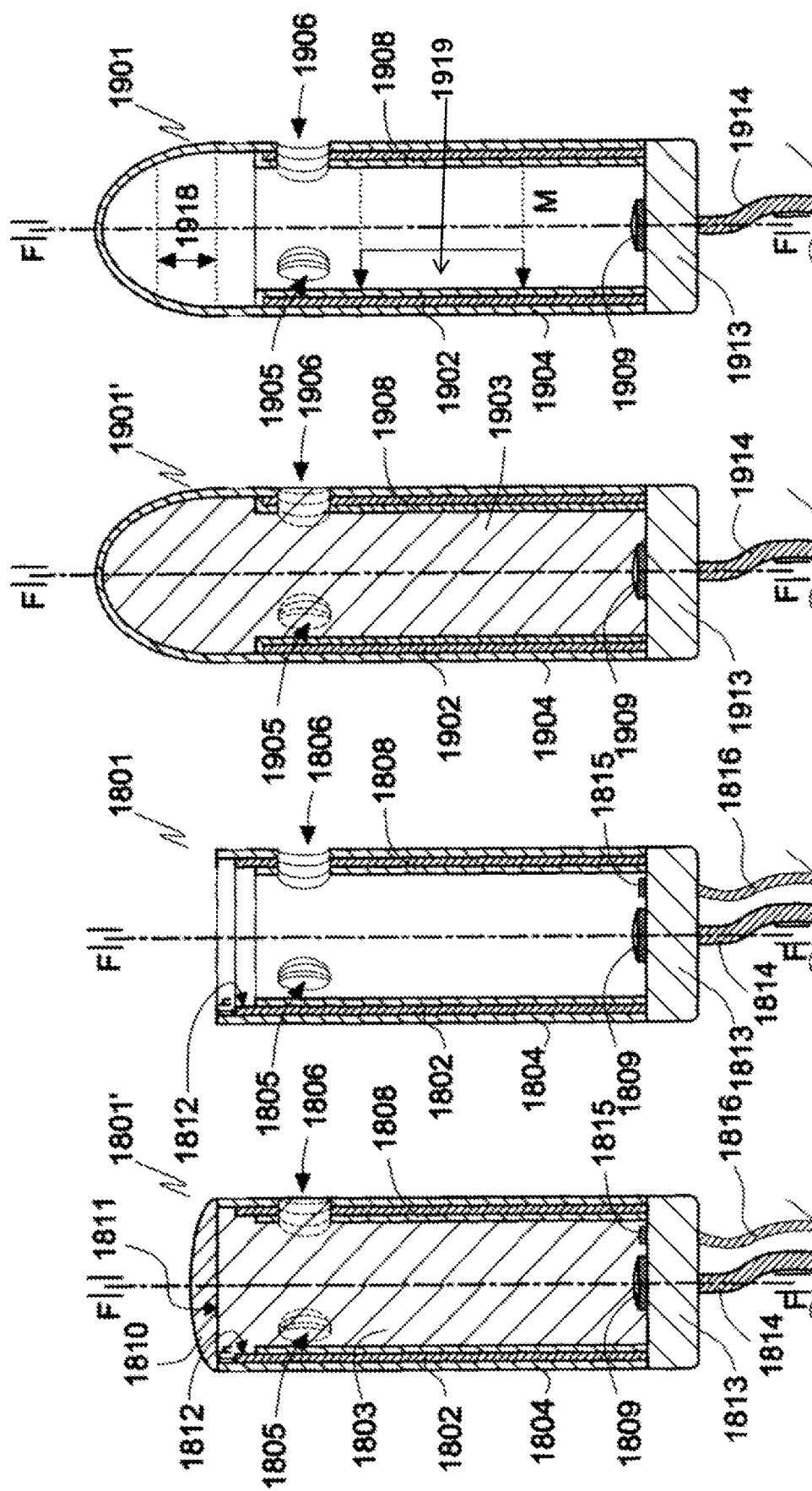

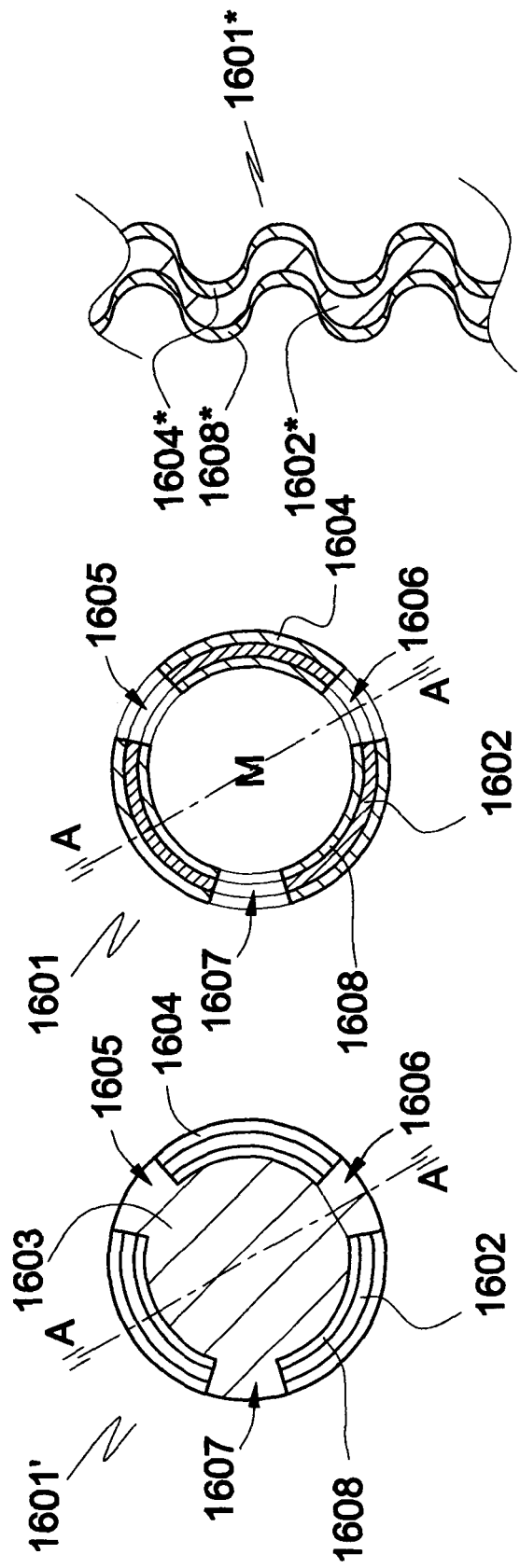

MEDICAL DEVICE COMPRISING AN ELECTRODE AND A LIGHT SOURCE

CROSS REFERENCE TO RELATED APPLICATIONS

The present application is a 35 U.S.C. § 371 National Phase conversion of PCT/SE2014/000152, filed Dec. 18, 2014, which claims benefit of Swedish Application No. 1300786-9, filed Dec. 20, 2013, the disclosures of which are incorporated herein by reference. The PCT International Application was published in the English language.

FIELD OF THE INVENTION

The present invention relates to a first device comprising a medical micro electrode and a micro light source for disposition in soft tissue, to a second device formed in tissue from the first device, to a method of producing the first device, and to the use of the devices. Furthermore the present invention relates to bundles and arrays comprising two or more first devices of the invention and to corresponding bundles and arrays of second devices disposed in soft tissue.

BACKGROUND OF THE INVENTION

Devices for implantation into soft tissue comprising electrodes, light sources, and combinations thereof in tissue of the central nervous system (CNS), have a wide field of application. In principle, brain nuclei can be recorded from or stimulated by such devices and their functions monitored. Of particular interest are multichannel devices for brain nuclei stimulation. By multichannel devices, groups of nuclei or even individual nuclei can be addressed separately. This allows a user to select those nuclei whose stimulation produces a therapeutic effect. Selective stimulation should produce a result superior to non-selective stimulation. Stimulation of the brain or spinal cord can be of particular value in situations when brain nuclei are degenerated or injured. A multichannel design may provide for efficient measurement of the effects of systemic or local drug administration or gene transfer to neurons of the brain and spinal cord. Monitoring brain activity through implanted devices can be used to control drug delivery locally or systemically or to control electrical stimulation of brain nuclei. By infecting neurons with gene vectors that cause the neuron to express radiation sensitive, in particular visible light sensitive ion channels it is possible to stimulate or inhibit neurons by radiation, in particular visible light. This is referred to as an optogenetic technique. By combining electrode means, radiation or visible light emission means and radiation or visible light detection means it is possible to record neuron activity evoked by radiation, in particular visible light.

An implanted device of this kind should affect the adjacent tissue as little as possible. Since the brain, the spinal cord, and peripheral nerves exhibit considerable movements caused by body movements, heart beats, and respiration, it is important that an implanted device is capable of following the movements of the tissue with as little as possible displacement relative to target tissue.

US 2011-0046148 A1 discloses a hybrid optical-electrical neural interface. The interface can include an array comprising a plurality of micro optrodes combining optical stimulation and optional electric stimulation.

US 2013-0253261 A1 discloses a method of sensing bioelectrical signals from a patient of a particular neurological condition using an implanted electrode combined with optical stimulation to cells transduced with a genetic agent of a viral vector to treat the condition.

US 2013-0237906 A discloses a liquid chrystal polymer-based electro-optrode neural interface comprising an integrated electrode and optrode.

OBJECTS OF THE INVENTION

A primary object of the invention is to provide device comprising a micro electrode and a micro light source for insertion into soft tissue, in particular one capable of subtly adapting to movements in surrounding tissue.

Another object of the invention is to provide a device of the aforementioned kind capable of stimulating single nerve cells or groups of nerve cells upon insertion into soft tissue;

A further object of the invention is to provide a device of the aforementioned kind capable of recording, upon insertion into soft tissue, optical and electrical signals originating from nerve cells;

An additional object of the invention is to provide bundles and array of the device;

Still another object of the invention is to provide a method for producing the insertable device of the invention;

Further objects of the invention will become apparent from the following summary of the invention, the description of preferred embodiments thereof illustrated in a drawing, and from the appended claims.

SUMMARY OF THE INVENTION

In this application "water insoluble" signifies insoluble in aqueous body fluid, that is, interstitial or extracellular fluid but also serum. "Flexible" signifies a degree of flexibility that allows displacement of a portion of the device by movement of tissue adjacent to that portion. Displacement of a portion of the device does not necessarily comprise displacement of the entire device. "Electrically insulating" signifies electrically insulating at voltages/currents used in treating of human nervous tissue. "Oblong" signifies a structure of a length greater by a factor of five or more, in particular of ten or more, than its diameter. "Swellable" means capable of forming a transparent gel on contact with aqueous body fluid accompanied by expansion of volume, such as by a factor of 1.1 or 1.2. "Porous" signifies permeable for aqueous body fluid and biomolecules dissolved therein.

According to the present invention is disclosed a medical device for insertion into soft tissue having a front or distal end and a rear or proximal end, comprising:
 a micro electrode;
 a micro light source capable of emitting light in a distal direction;
 a stiffening element comprising one of:
  a) a material dissolvable or degradable in aqueous body fluid in an amount sufficient to make the stiffening element collapse in contact with aqueous body fluid;
  b) a material swellable in aqueous body fluid to form a transparent gel;
 a coat of a flexible non-conducting polymer material on the stiffening element preventing or at least delaying contact between the electrode and soft tissue upon collapse or swelling of the stiffening element, the coat having a distal opening allowing light emitted from the light source to leave the device upon said collapse or swelling;
 a base disposed at the proximal end of the device.

It is preferred for the base to be of an electrically non-conducting material or to consist to 80% or 90% or more of such a material. It is preferred for the base to be of about circular form, such as the form of a flat cylinder. The base is preferably rigid.

It is preferred for the electrode, the light source and/or the coat of flexible material to be firmly attached to the base and to extend from the distal face of the base in a distal direction. It is preferred for the electrode and the light source to extend from the distal face for a smaller distance than the flexible coat.

Any miniature light source can be used but the use of an LED or a micro laser is preferred. In the present the invention "light source" comprises an optical fiber which receives, at its one end, light from a source which may or may not be comprised by the device and which fiber emits the received light at its other, distal end. The light emitted from the light source is preferably visible light, in particular monochrome light, such as red light, but may also be infrared light.

The micro electrode of the invention comprises or consists of a metal or a metal alloy or an electrically conducting polymer or carbon. Preferred metals include aluminum, silver, gold, iridium, platinum, and their alloys. The micro electrode can have the form of a straight or curved rod or a layer on an optical fiber or on the face of the polymer coat facing the stiffening element. The micro electrode is preferably electrically insulated except for a portion extending from its distal end in a proximal direction. Electrode insulation is provided by a layer of lacquer or polymer on the electrode.

It is preferred for the device for insertion into soft tissue to be of about rotationally symmetric form, in particular of about cylindrical form, in respect of a central longitudinal axis. The flexible, non-conducting polymer coat and the stiffening element are also preferred to be of about rotationally symmetric form, in particular of cylindrical form. It is preferred for the distal end of the electrode and/or of the optical fiber to be withdrawn from the distal opening in a proximal direction. It is also preferred for the electrode to be electrically insulated except for at its distal tip or end, or a portion extending from its distal tip or end in a proximal direction.

According to a first preferred aspect of the invention the electrode is electrically shielded by an electrically conducting layer kept at earth potential or animal ground potential integrated into the flexible polymer coat or attached to one face of the flexible polymer coat and covered by an electrically insulating layer.

According to a second preferred aspect of the invention the stiffening element comprises or consists of a carbohydrate and/or proteinaceous material and/or a mixture thereof. It is also possible to use other biocompatible gel forming polymers such as polyethylene glycol (PEG) and polypropylene glycol (PPG).

Upon insertion into soft tissue and dissolution, degradation or swelling of its stiffening element the device for insertion into soft tissue is extendable in a longitudinal (proximal-distal) direction, in particular by a portion of its polymer coat being extendable. To be extendable the flexible polymer coat need not be of a resiliently flexible material. The polymer coat, which is preferably non-resilient or only faintly resilient, is made extendable by providing it or at least a portion of it in a bellows shaped configuration. Thus, according to a third preferred aspect of the invention the flexible polymer coat of the device for insertion into soft tissue is bellows-shaped and the stiffening element does reflect this shape.

According to a fourth preferred aspect of the invention the device for insertion into soft tissue comprises a microprocessor control unit. The microprocessor can control one or more of electrode voltage; electrode potential including its variation over time; emission of light over time. The microprocessor unit may be capable of detecting voltage phenomena emanating from tissue structures, in particular neurons. In addition, the microprocessor unit can control a radiation sensor, in particular one for visible and/or near infrared light. The radiation sensor is preferably mounted at the base. It can detect light reflected from tissue structures, such as neurons, and/or fluorescent light emitted from such structures.

According to a fifth preferred aspect of the invention the stiffening element comprises two or more cylindrical sections of different composition disposed adjacent to each other in a longitudinal (distal-proximal) direction. At least one section thereof can comprise a pharmacologically active agent, in particular an agent affecting neurons or glia cells, such as dopamine, dopamine agonist, dopamine antagonist, serotonin, serotonin antagonist. In another preferred embodiment the pharmacologically active agent is one having anti-inflammatory properties. In still another preferred embodiment the pharmacologically active agent is selected from neurotropic factor, in particular BDNF and NGF. The pharmacologically active agent also comprises genes.

According to a sixth preferred aspect of the invention the stiffening element comprises two sections of different composition disposed adjacent to each other in a radial direction. It is preferred for at least one section thereof to comprise a pharmacologically active agent, in particular an agent affecting neurons, such as dopamine, dopamine agonist, dopamine antagonist, serotonin, serotonin antagonist, neurotropic factors such as BDNF, NGF, and genes.

According to a seventh preferred aspect of the invention the device for insertion into soft tissue comprises a reservoir filled with a solution of a pharmacologically active agent, in particular an aqueous solution. The reservoir is disposed in a proximal section of the device, in particular at or near its proximal end. Dissolution or degradation of the stiffening element puts the reservoir in communication with soft tissue into which the device has been inserted. The communication is provided by the body fluid filled column delimited by the flexible polymer coat through which the solution of pharmacologically agent can be forced by applying pressure to the reservoir or through which the pharmacologically agent can diffuse so as to leave the column at its open distal end.

According to an eight preferred aspect the device for insertion into soft tissue comprises, at its rear end, a means for wireless communication with an external control unit and/or a non-wireless means for electrical and/or optical communication with such unit, such as one or more electrically insulated electrical conductors and/or one or more optical fibers.

According to another preferred embodiment, the device of the invention comprises a radiation sensor, in particular one sensitive to visible and/or near infrared light. It is preferred for the sensor to be mounted in the base.

According to still another preferred aspect of the invention the distal opening is selected from axial distal opening and radial distal opening. In a first variety of the proto device of the invention and a corresponding device of the invention a distal opening is covered by a sheet of translucent polymer material, which is preferably as flexible or is more flexible than the polymer coat. Illumination of soft tissue adjacent to an radial distal opening can occur directly by a beam of light emitted from the radiation source or indirectly by such beam being reflected one more times from an inner wall face of the device before leaving the inner void M through the radial opening. To enhance the intensity of the portion of the beam escaping through a radial distal opening section(s) of the inner face of the wall can be made more reflective by, for instance, using an appropriate polymer material of high reflectivity and/or by applying a high reflectivity polymer coat on an inner face of the wall. A high reflectivity polymer coat can comprise microscopic inorganic or organic particles of high reflectivity, such as $TiO_2$ or platinum micro particles in the micrometer range.

The device for therapeutic and/or diagnostic use of the invention is capable of being used for one or more of: a) emission of light into surrounding soft tissue; b) detection of light emitted from surrounding soft tissue; c) electrical stimulation of surrounding tissue structures; d) detection of electrical signals emitted from surrounding soft tissue.

The device for therapeutic and/or diagnostic use of the invention disposed in soft tissue has a front (distal) end and a rear (proximal) end, and comprises:
- a micro electrode;
- a micro light source capable of emitting light in a distal direction;
- an about cylindrical coat of a flexible non-conducting polymer material comprising a distal opening allowing light emitted from the light source to leave the device, the coat delimiting an about cylindrical space filled with aqueous body fluid and/or a transparent gel;
- a base disposed at the proximal end of the device.

Upon insertion into soft tissue the device of the invention for insertion into soft tissue is transformed into a device for therapeutic and/or diagnostic use by dissolution, degradation or swelling of its stiffening element. Except for substitution of the stiffening element by aqueous body fluid and/or a transparent gel, which renders the device flexible and capable of adapting to movements of adjacent tissue, and the optional cap of body fluid soluble material disposed on the distal face of the device for insertion into soft tissue, the device for therapeutic and/or diagnostic use of the invention shares most or all features of the former, its design and structure thus being identified.

According to the invention is also disclosed the use of the device for therapeutic and/or diagnostic use for providing optical and/or electrical stimulation to structures of soft tissue such as neurons, for recording electrical signals emanating from such structures, for lesioning such structures, for combined drug delivery, for recording of nerve cell signals and for nerve cell stimulation.

According to the invention is furthermore disclosed a method of disposing the device for therapeutic and/or diagnostic use of the invention in relation to a selected structure in the tissue, comprising:
- inserting a device of the invention for insertion into soft tissue with its distal end foremost to make it take up a first position;
- maintaining the device in the first position until the stiffening element has been dissolved, degraded or swelled to form a transparent gel;
- making the light source emit light in the direction of the selected tissue structure;
- monitoring the position of the selected tissue structure by detecting light reflected from the structure;
- displacing the device in respect of the selected tissue structure to make it assume a second position.

The invention will now be explained in greater detail by reference to a number of preferred embodiments illustrated in a rough drawing, which is only intended to show the principles of the invention. The drawings are not to scale. Radial dimensions are greatly exaggerated.

DESCRIPTION OF THE FIGURES

All figures illustrate embodiments of the invention. In some of them the combination of light source and electrode of the invention is only shown schematically to illustrate its disposition in the prestage device, the proto device or the device of the invention. It should be understood that each of the embodiments of combination of electrode and light source illustrated in FIGS. 1h-1s

FIGS. 1a through 1g illustrate, in a more general manner, distal terminal portions of a prestage, a proto device and a device of the invention. In particular, it is shown in:

FIG. 1a a prestage of the device of the invention, in a longitudinal axial section corresponding to axial section B-B in FIG. 1e;

FIG. 1b a distal terminal portion of the prestage of FIG. 1a, in the same view;

FIG. 1c a distal terminal portion of a proto device of the invention manufactured from the prestage of FIGS. 1a, 1b, in the same view as in FIG. 1a;

FIG. 1d a distal terminal portion of the proto device of FIG. 1c upon insertion into soft tissue and partial dissolution of its stiffening element, in the same view as in FIG. 1a;

FIGS. 1e, 1f, a distal terminal portion of a first embodiment of the device of the invention (FIG. 1e) and a major portion of the device (FIG. 1f) formed from the proto device of FIGS. 1c, 1d by contact with aqueous body fluid, in the same view as in FIG. 1a;

FIG. 1g a radial section A-A (FIG. 1b) of the proto device of FIG. 1c;

FIG. 1h a distal terminal portion of the prestage of a second embodiment of the proto device of the invention, in a longitudinal axial section B*-B*;

FIG. 1i the prestage of FIG. 1h, in a radial section A*-A*;

FIG. 1m' the proto device of FIG. 1l', in radial section A*-A*;

FIG. 1l, 1m a distal terminal portion of a first embodiment of the device of the invention, formed from the proto device of FIGS. 1l', 1m' by contact with aqueous body fluid, and in the same view;

FIG. 1l* a variation of the proto device of FIGS. 1l', 1m', and in the same view as in FIG. 1l';

FIG. 1j a distal terminal portion of a prestage of a second embodiment of the proto device of the invention, in an axial section B*-B* (FIG. 1i);

FIG. 1k the prestage of FIG. 1j, in a radial section A*-A*;

FIG. 1o' the proto device of FIG. 1n, in a radial section A-A;

FIG. 1n a distal terminal portion of a second embodiment of the device of the invention formed from the proto device of FIGS. 1n', 1o' upon insertion into soft tissue, in an axial section;

FIG. 1o the device of FIG. 1n', in a radial section A-A;

FIG. 1n* a variation of the proto device of FIGS. 4n', 4o', in a the same view as in FIG. 1n;

FIG. 1p' a distal terminal portion of a third embodiment of the proto device of the invention, in an axial section B-B (FIG. 1i);

FIG. 1q' the proto device of FIG. 1p', in a radial section A*-A*;

FIG. 1p a distal terminal portion of a third embodiment of the device of the invention, formed from the proto device of FIGS. 1p', 1q' upon contact with aqueous body fluid, in an axial section corresponding to that of FIG. 1i);

FIG. 1q the embodiment of FIG. 1p, in a radial section A*-A*;

FIG. 1r' a distal terminal portion of a fourth embodiment of the proto device of the invention, in an axial section;

FIG. 1s' the proto device of FIG. 1r', in a radial section A-A;

FIG. 1r a distal terminal portion of a fourth embodiment of the device of the invention, formed from the proto device of FIG. 1r' upon contact with aqueous body fluid, in an axial section;

FIG. 1s the device of FIG. 1r, in a radial section A-A;

FIG. 2 a fifth embodiment of the proto device of the invention, in an axial section;

FIG. 3 a sixth embodiment of the proto device of the invention, in an axial section;

FIG. 4 a distal terminal portion of an seventh embodiment of the proto device of the invention, in an axial section;

FIG. 5 a distal terminal portion of an eight embodiment of the proto device of the invention, in an axial section;

FIGS. 9a-9c a bundle of four proto devices of the invention, in a longitudinal section R-R (9a) and two radial sections O-O and P-P (9b, 9c);

FIG. 15 a thirteenth embodiment of the proto device of the invention, in an axial section;

FIG. 16 a fourteenth embodiment of the proto device of the invention, in an axial section comprising, in addition to the features of the thirteenth embodiment radiation sensing means;

FIG. 17 a fifteenth embodiment of the proto device of the invention in an axial section A-A (FIG. 29), comprising an axial distal opening and three lateral distal openings;

FIG. 18 a device of the invention formed from the proto device of FIG. 17 upon implantation into soft tissue, in an axial section A-A (FIG. 30);

FIG. 19 a sixteenth embodiment of the proto device of the invention in an axial section corresponding to that of the embodiment of FIG. 17, comprising three lateral distal openings;

FIG. 20 a device of the invention formed from the proto device of FIG. 19 upon implantation into soft tissue, in an axial section corresponding to that of the embodiment of FIG. 18;

FIG. 21 a seventeenth embodiment of the proto device of the invention in an axial section corresponding to that of the embodiment of FIG. 17, comprising an optical sensor;

FIG. 22 a device of the invention formed from the proto device of FIG. 21 upon implantation into soft tissue, in an axial section corresponding to that of the embodiment of FIG. 18;

FIG. 23 an eighteenth embodiment of the proto device of the invention in an axial section corresponding to that of the embodiment of FIG. 17, comprising a light reflecting inner wall section and a body fluid permeable wall section;

FIG. 24 a device of the invention formed from the proto device of FIG. 23 upon implantation into soft tissue, in an axial section corresponding to that of the embodiment of FIG. 18;

FIG. 29 the proto device of FIG. 17, in a radial section B-B;

FIG. 30 the device of FIG. 18, in a corresponding radial section;

FIG. 31 a bellows-type axial section of a flexible wall of a device of the invention consisting of the layer combination flexible coat/flexible electrode layer/flexible insulation layer.

DESCRIPTION OF PREFERRED EMBODIMENTS

Example 1

Figure 1L:
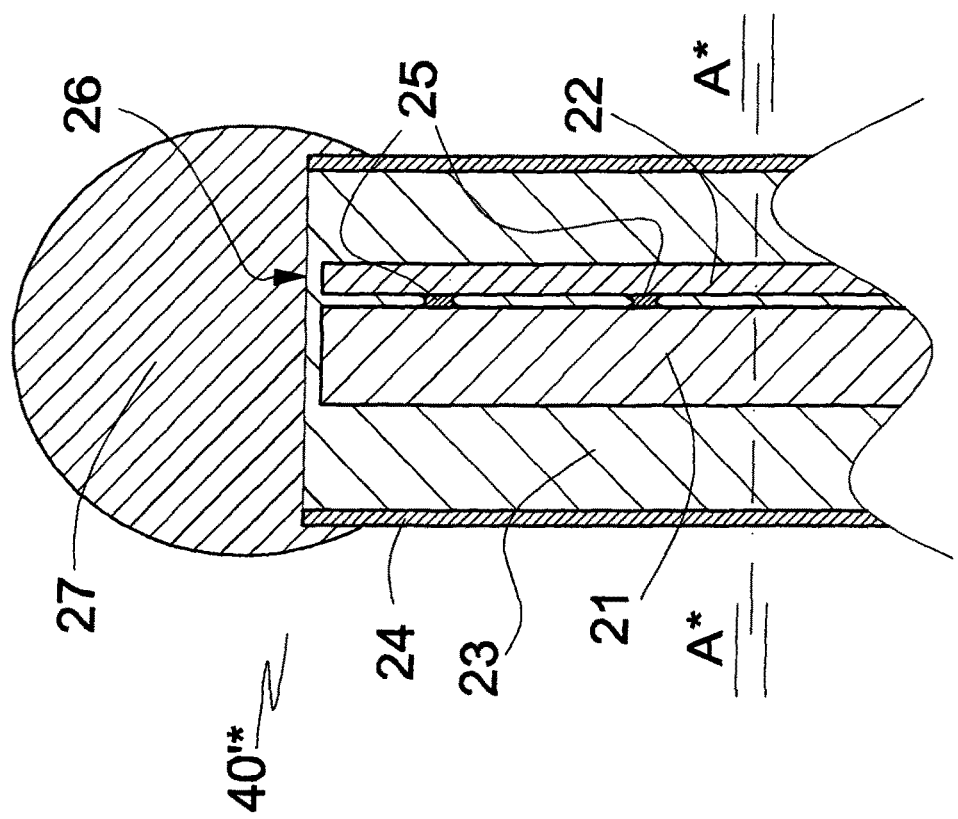
FIG. 1l' a distal terminal portion of a first embodiment of the proto device of the invention, manufactured from the prestage of FIGS. 1h, 1i, in an axial section corresponding to section B*-B* in FIG. 1i.

General Disposition of a Combination of Micro Electrode and Optical Fiber in a Prestage Device, a Proto Device and a Device of the Invention FIGS. 1a, 1b show axial sections of a terminal portion and a major portion including the terminal portion of a prestage device 1" of the composition. The multi-S-formed portion extending from the terminal portion is extendable in a distal/proximal direction. The terminal portion comprises a blunt distal tip 9. A combination 2 of optical fiber and electrode is schematically rendered. The combination 2 is centered in the distal and main portions. The terminal portion is rotationally symmetric, cf central axis B-B in FIG. 1f. The combination of electrode and optical fiber 2 is enclosed by a stiffening element or layer 3, which is also rotational symmetric at least in the straight distal terminal portion. The stiffening element 3 is of a material dissolvable in aqueous body fluid including water or degradable by the fluid or water, and is preferably of a biocompatible carbohydrate and/or proteinacious material such as glucose and albumin. Alternatively, the stiffening element 3 is of a biocompatible material gelling by contact with aqueous body fluid, such as gelatin or hyaluronic acid or a mixture of gelatin or hyaluronic acid with carbohydrate and/or proteinacious material. In a gelled state the gelling material is translucent. A thin layer 4 of a flexible, electrically insulating material such as parylene C is disposed on the stiffening element so as to enclose it completely.

FIG. 1c illustrates the distal terminal portion of a proto device 1' of the invention obtained by radially cutting the prestage device 1" in plane A-A. Reference numbers 2, 3, 4 identify the same features as in FIGS. 1a, 1b. By cutting the prestage device 1" a circular, flat terminal face 6 illustrated by FIG. 1g is produced.

FIG. 1d shows a state of the proto device 1' upon insertion into soft tissue for a short period of time. By contact with aqueous body fluid a terminal portion of the stiffening element 3 has been dissolved or degraded or transformed to a translucent gel, the transformed portion being identified by 8.

In FIGS. 1e and 1f the entire layer of stiffening element 3 has been transformed. Reference numbers 2-4 and 8 retain their meaning explained above.

Example 2

Prestage Device, Proto Device and Device of the Invention Comprising a First Combination of Micro Electrode and Optical Fiber FIGS. 1h and 1i illustrate axial B*-B* and radial A*-A* sections of the distal terminal portion of a prestage device 40" comprising a first combination of micro electrode 22 and optical fiber 21. The fiber 21 and the electrode 22 are disposed in parallel and attached to each other by permanent adhesive bridges 25. The combination of optical fiber 21 and electrode 22 is enclosed by a layer or element 23 of a stiffening material. The optical fiber 21 has polished flat distal face 31 disposed at about the same radial level as the distal end of the electrode 22.

By cutting the prestage device 40" radially in a plane A'-A' distally of the face 31 the proto device 40' illustrated in FIGS. 1l', 1m' is formed, in which the reference numbers of FIGS. 1h, 1i retain their meaning.

Upon insertion of the proto device 40' with its distal end foremost into soft tissue, the stiffening element 23 is dissolved or degraded by contact with aqueous body fluid 8 and substituted by it or is transformed into a translucent gel 28, FIGS. 1l, 1m. Cutting the prestage device 40" distally of the end face 31 of the optical fiber 21 and the distal end or tip of the electrode 22 the fiber 21 and the electrode 22 are disposed withdrawn from the distal face 26 of the stiffening element 23 and of the distal circular rim 26 (FIG. 1l) of the flexible polymer coat 24, respectively, thereby preventing or at least delaying contact of the electrode 22 and the optical fiber 21 of the device of the invention with surrounding tissue.

In FIG. 1l* a variety 40'* of the proto device 40' is shown, of which the distal face 26 is covered by a cap 27 of a water soluble material such as glucose or a mixture of glucose with lactose or gelatin. The function of the cap 27 is to facilitate insertion of the proto device into soft tissue and to delay contact of the electrode 22 with surrounding tissue.

Example 3

Prestage Device, Proto Device and Device of the Invention Comprising a Second Combination of Micro Electrode and Optical Fiber FIGS. 1j and 1k illustrate axial B-B and radial A'-A", A-A sections of the distal terminal portion of a prestage device 50" comprising a second combination of micro electrode 22 and optical fiber 21 enclosed by a layer or element 23 of stiffening material. The electrode 22 has polished flat distal face 31 and is enclosed by an electrically conducting layer 22 forming an electrode. The distal end of the electrode layer 22 and the distal face 31 of the optical fiber 21 are disposed at the same radial level.

By cutting the prestage device 50" radially in a plane A-A distally of the face 31 of the proto device 40' illustrated in FIGS. 1l', 1m' is formed, in which the reference numbers of FIGS. 1h, 1i retain their meaning.

Upon insertion of the proto device 50' with its distal end foremost into soft tissue, the stiffening element 23 is dissolved or degraded by contact with aqueous body fluid 8 and substituted by it or is transformed into a translucent gel 28, FIGS. 1l, 1m. Cutting the prestage device distally of the end face 31 of the optical fiber and of the electrode tip disposes the end face 31 withdrawn from the distal face 26 of the stiffening element 23 and of the distal circular rim 26 (FIG. 1l) of the flexible polymer coat 24, thereby preventing or at least delaying contact of the electrode 22 and the optical fiber 21 with surrounding tissue.

Figure 1N:
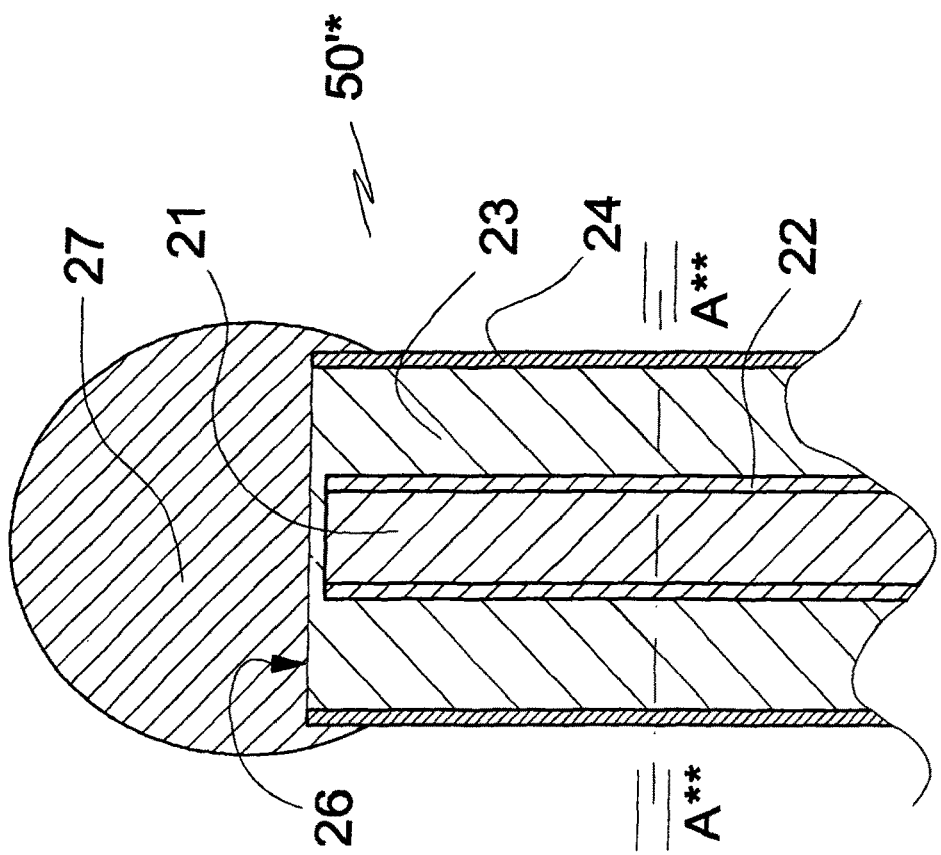
FIG. 1n' a distal terminal portion of a second embodiment of the proto device of the invention, manufactured from the prestage of FIGS. 1j, 1k in a radial plane A"-A" to remove its rounded tip section, in a longitudinal axial section B*-B* (FIG. 1i)

In FIG. 1n'* a variety 50'* of the proto device 50' is shown, the distal face 26 of which is covered by a cap 27 of a water soluble material such as glucose. The function of the cap 27 is to facilitate insertion into soft tissue.

Example 4

Prestage Device, Proto Device and Device of the Invention Comprising a Third Combination of Micro Electrode and Optical Fiber FIGS. 1p', 1q' illustrate axial B*-B* and radial A*-A* sections of the distal terminal portion of a proto device 60' of the invention, comprising a third combination of micro electrode 22 and optical fiber 21. The fiber 21 and the electrode 22 are disposed in parallel and attached to each other by permanent adhesive bridges 25. The combination of optical fiber 21 and electrode 22 is enclosed by a layer or element 23 of a stiffening material, which is in turn enclosed by a coat 24 of flexible polymer material such as Parylene C. The optical fiber 21 has polished flat distal face 31 disposed at about the same radial level as the distal end of the electrode 22. Except for a distal end portion the electrode 22 is electrically insulated by a lacquer coat 29. The proto device 60' has been produced from a corresponding prestage device (not shown) in a manner described in Examples 2 and 3.

Upon insertion of the proto device 60' with its distal end foremost into soft tissue, the stiffening element 23 is dissolved or degraded by contact with aqueous body fluid 8 and substituted by it or is transformed into a translucent gel 28, to form a third embodiment 60 of the device of the invention, FIGS. 1p, 1q.

Example 5

Prestage Device, Proto Device and Device of the Invention Comprising a Fourth Combination of Micro Electrode and Optical Fiber FIGS. 1r', 1s' illustrate axial and radial A\-A\ sections of the distal terminal portion of a proto device 70' of the invention, comprising a fourth combination of micro electrode 22 and optical fiber 21. The combination of micro electrode 22 and optical fiber 21 is enclosed by a layer or element 23 of stiffening material. The optical fiber 21 has a polished flat distal face 31. It is enclosed by an electrically conducting layer 22 forming the electrode. Except for a portion 33 extending proximally from its distal end the electrode layer 22 is covered by an insulating lacquer 32. The lacquer 32 is disposed between the electrode layer 22 and the stiffening element 23. The distal end of the electrode layer 22 and the distal face 24 of the optical fiber 21 are disposed at the same radial level.

Upon insertion of the proto device 70' with its distal end foremost into soft tissue, the stiffening element 23 is dissolved or degraded by contact with aqueous body fluid 8 and substituted by it or is transformed into a translucent gel 28. Thereby a corresponding device 70 of the invention is formed, FIGS. 1r, 1s.

Example 6

Fifth Embodiment of the Proto Device of the Invention

The proto device 201' of FIG. 2 is about rotationally symmetric in respect of a central longitudinal axis D-D. The proto device 201' comprises, in addition to a combination of optical fiber and electrode 202, a stiffening element 203 of a water dissolvable or degradable material and a coat 204 of a flexible, water insoluble polymer material on the stiffening element 203. The proto device 201' is provided with a rounded cap 207 on its front end. The purpose of the cap 207 is to minimize tissue damage caused by inserting the proto device 201' into soft tissue. The material of the cap 207 is one that is readily dissolvable in body fluid, that is, within a couple of minutes, but which is different from water soluble material of the stiffening element 203. The electrode and the optical fiber are electrically and optically, respectively, connected with a control unit 230 disposed at the proximal end of the proto device 201'. The control unit is of the same kind as that of the following example.

Example 7

Sixth Embodiment of the Embodiment of the Proto Device of the Invention

The proto device 301' of FIG. 3 is about rotationally symmetric in respect of a central longitudinal axis E-E. The proto device 301' comprises, in addition to a combination of optical fiber and electrode 302, a stiffening element 303 and a coat 304 of a flexible, water insoluble polymer material on the stiffening element 303. The proto device 301' is provided with a rounded cap 307 on its front end. The purpose of the cap 307 is to minimize tissue damage caused by inserting the proto device 301' into soft tissue. The material of the cap 307 is identical with the material of the stiffening element 303. The electrode and the optical fiber are electrically and optically, respectively, connected with a control unit 330 disposed at the proximal end of the proto device 301'. The control unit 330 can be of various kinds and for various purposes, such as for controlling the current and voltage of power fed to the electrode and/or for recording and/or transmitting electric signals received from the electrode and/or for emitting radiation into the optical fiber or receiving radiation emanating from the tissue through the optical fiber and detecting it.

Example 8

Seventh Embodiment of the Proto Device of the Invention

Of the seventh embodiment 401' of the proto device of the invention illustrated in FIG. 4 is only shown a distal terminal portion. The proto device 401' is rotationally symmetric about a central longitudinal axis J-J and comprises an optical fiber 421, an electrically conducting coat 422 forming an electrode on the fiber 421, a stiffening layer or element 423 on the electrode 422 and a second coat 424 of flexible, water insoluble polymer material on the stiffening element 423. A distal terminal section of the electrode layer 422 has the form of a brush 422\* of tiny metallic fibers extending in a radial direction from the layer 422 so as to provide for a large electrode tip surface. Except for the brush section 422\* the electrode 422 is insulated by a lacquer (not shown). The optical fiber has a distal terminal flat face 431 disposed in the same radial plane as the distal rim of the flexible polymer coat 424.

Example 9

Eight Embodiment of the Proto Device of the Invention

Of the eight embodiment 501' of the proto device of the invention illustrated in FIG. 5 is only shown a distal terminal portion. The proto device 501' is rotationally symmetric about a central longitudinal axis K-K and comprises an optical fiber 521, an electrically conducting coat 522 forming an electrode on the fiber 521, a stiffening layer or element 523 on the electrode 522 and a coat 524 of flexible, water insoluble polymer material on the stiffening element 523. An electrically conducting layer 533 is provided on the flexible polymer coat 524 and is covered by a coat 524' of same material as the flexible polymer coat 524, so as to be fully enclosed by the insulating coats 524, 524'. The conducting layer 533 is kept on earth potential for shielding the electrode 522. The optical fiber 521 has a distal terminal flat face 531 disposed in the same radial plane as the distal rim of the flexible polymer coat 524.

Example 10

Ninth Embodiment of the Proto Device of the Invention

Figure 6:
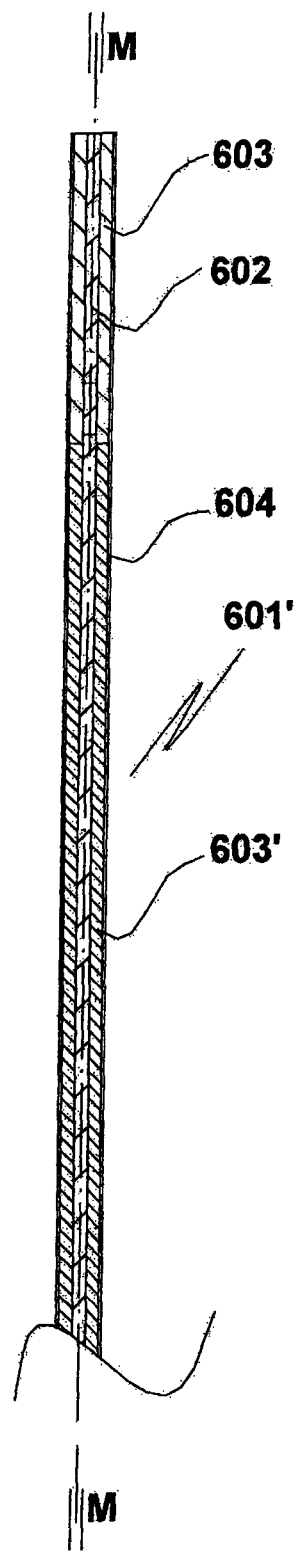
FIG. 6 a distal terminal portion of a ninth embodiment of the proto device of the invention, in an axial section.

The proto device 601' of cylindrical form (central axis M-M) of the invention of FIG. 6 is similar to that of FIG. 1c except for the water soluble stiffening element consisting of two sections, a frontal (distal) section 603 and a proximal section 603' extending rearwards from the distal end of the frontal section 603. Elements 602, 604, 606 correspond functionally to elements 2, 4 and 6 of the embodiment of FIG. 1c. By providing two or more water soluble stiffening element sections joining each other in radial plane(s) it is possible to vary its dissolution profile more than what is possible with a one-section stiffening element.

Example 11

Tenth Embodiment of the Proto Device of the Invention

Figure 7:
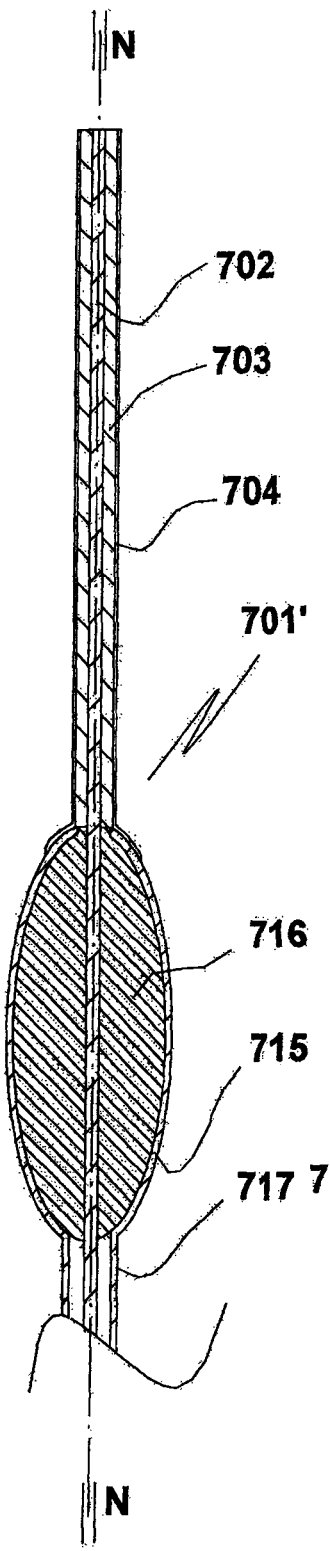
FIG. 7 a distal terminal portion of a tenth embodiment of the proto device of the invention comprising a drug delivery compartment, in an axial section.
Figure 8:
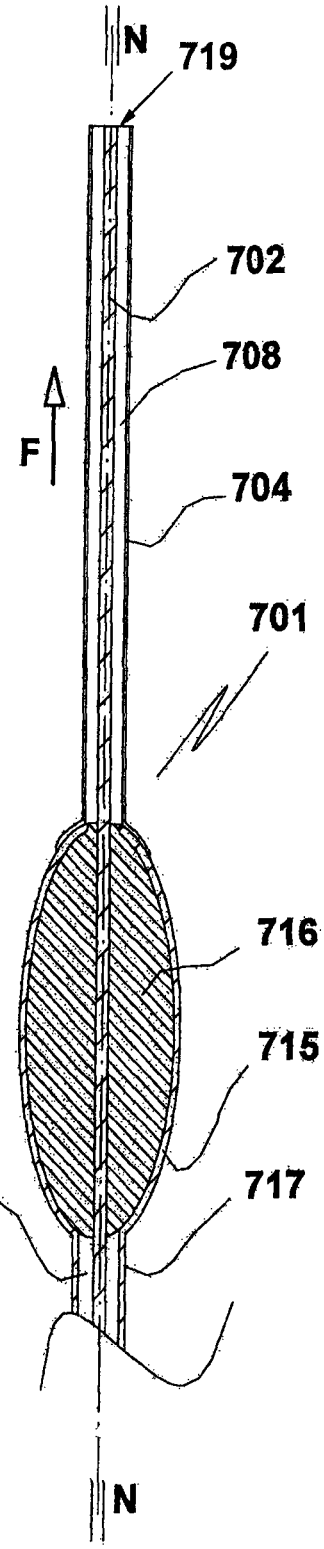
FIG. 8 a tenth embodiment of the device of the invention corresponding to the proto device of FIG. 7, in an axial section.

The tenth embodiment of the proto device of the invention 701' of FIG. 7 (axial section N-N) comprises a front portion functionally corresponding to that of the embodiment of FIG. 1c, elements 702, 703, 704, corresponding to elements 2, 3, and 4, respectively. The water soluble material of the stiffening element 703 does not extend along the entire proto device 701' but only over a portion thereof extending rearwards from its distal end. At the rear end of the stiffening element 703 a bulged container 715 of polymer material through which the combination of optical fiber and electrode 702 extends centrally is joined. The rear end of the container 715 of a polymer material such as parylene or silicone rubber is joined to a stiff polymer tube 717 through which the combination of optical fiber and electrode 702 further extends. The stiff tube 717 is so dimensioned that a tubular void 718 is formed between it and the container 715. The container 715 is filled with a porous, water insoluble material 716, for instance silica. A pharmacologically active agent, such as dopamine, is adsorbed on the porous material 716. By dissolution of the water soluble stiffening agent 703 by aqueous body fluid entering through the distal terminal opening 719 the void between the combination of optical fiber and electrode 702 and the flexible coat 704 of water insoluble polymer material becomes filled with body fluid. By this process the proto device of FIG. 7 is transformed to the device 701 of FIG. 8). By provision of a controlled forward flow F of saline in the void 718 of tube 717 dopamine adsorbed on the porous material 716 is dissolved and diffuses into the void 708 and, from there, through the distal terminal opening 719 into adjoining tissue to exert its effect on biological structures, such as neurons, the electrical activity of which can be monitored by the electrode and which can be irradiated by radiation conducted by the optical fiber of the combination of optical fiber and electrode 702.

Example 12

Bundle of Proto Devices of the Invention

In the bundle 800' of four proto devices 801a' through 801d' of FIG. 9a (section R-R), 9b (section O-O) and 9c (section P-P) the proto devices are disposed in parallel and mounted in through bores of a cylindrical base 820. Each of the proto devices 801a', 801b', 801c', 801d' comprises a central combination of optical fiber and electrode 802a, 802b, 802c, 802d, a water soluble stiffening element or layer 803a, 803b, 803c, 803d on each of the combinations of optical fiber and electrode 802a, 802b, 802c, 802d and a flexible water-insoluble polymer coat 804a, 804b, 804c, 804d on the corresponding stiffening element 803a, 803b, 803c, 803d. The proto devices 801a', 801b', 801c', 801d' are arranged symmetrically in respect of a central bundle axis Q-Q. Proximal sections 810a, 810c of the optical fibers and electrical conductors of the bundle are connected with a control unit (not shown).

Each of the various proto devices of the invention described in the preceding embodiments can be bundled to form a bundle of proto devices of the invention. A bundle of proto devices of the invention can comprise two or more different proto devices of the invention. By insertion of a bundle of proto devices of the invention into soft tissue a corresponding bundle of devices of the invention is formed by dissolution or degradation of the water soluble or degradable stiffening elements.

To facilitate insertion into soft tissue, the bundle of proto devices of the invention can be incorporated into a shell of a water soluble material (not shown). The shell has a sharp of blunt front end and is preferably rotationally symmetric about the bundle axis Q-Q and extends to the base 820.

Example 13

First Embodiment of an Array of Bundles of Proto Devices of the Invention

Figures 10, 11:
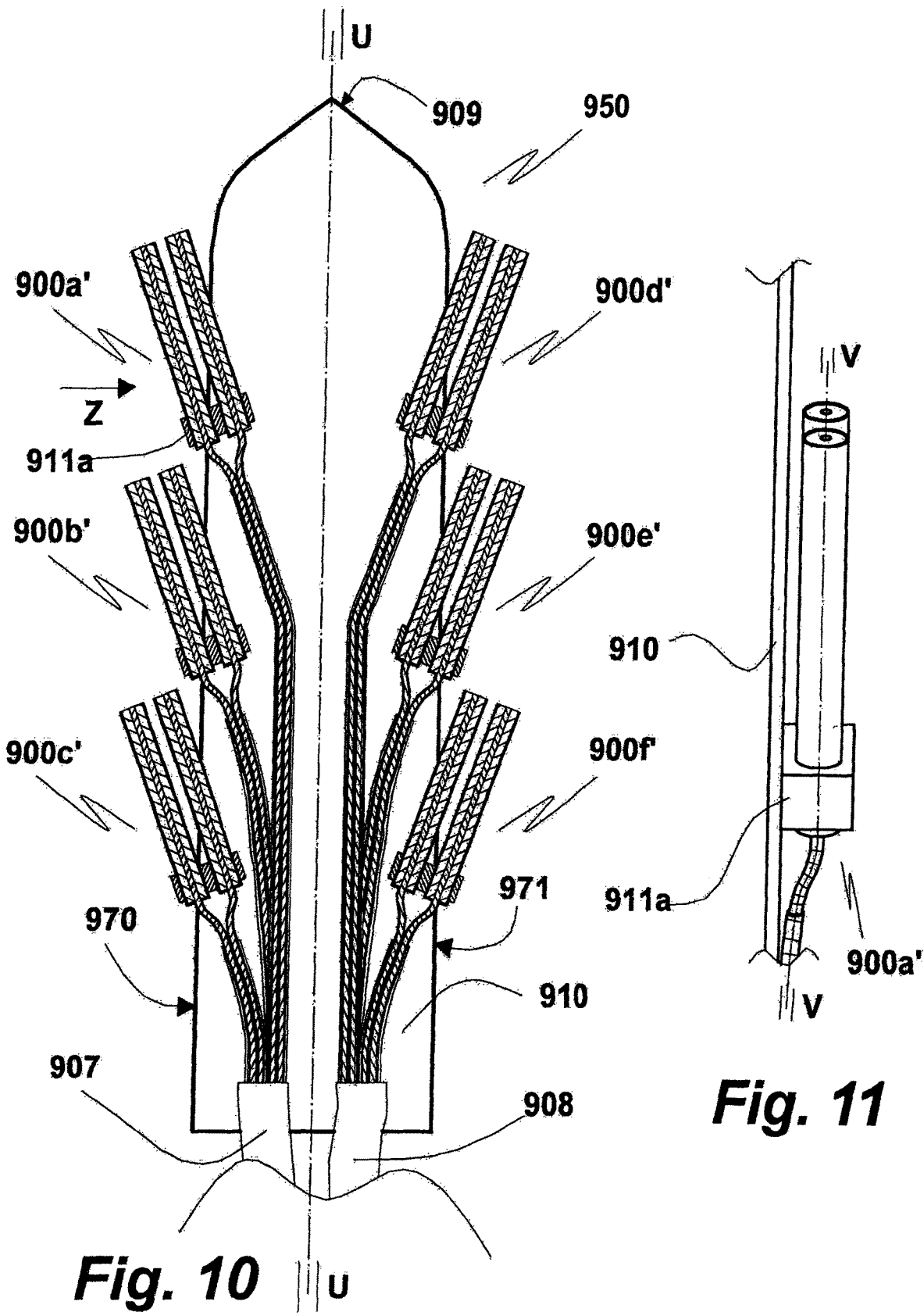
FIGS. 10, 11 an array comprising six bundles, each bundle comprising two proto devices of the invention, in a longitudinal section (FIG. 10) and a corresponding bundle in a perspective view (FIG. 11)

The array 950 of the invention shown in FIG. 10 (section V-V) comprises six bundles 901'a, 902'a, 903'a, 904'a, 905'a, 906'a of proto devices of the invention. Each bundle comprises a pair of proto devices. Each of the bundles 900a', 900b', 900c', 900d', 900e', 900f' is mounted at its rear end in a bundling holder (FIG. 11). Only the holder 911a for bundle 900a' is specifically identified in FIG. 11. The bundling holders 911 are mounted by gluing on an oblong, about rectangular flat base 910 with a pointed front end 909. The base 910 is preferably of a biocompatible polymer material like polypropylene, polyacrylate or polycarbonate. The holders 911a are mounted symmetrically in respect of the long base axis U-U so that three of the bundles 900a', 900b', 900c' of proto devices are mounted at the left hand long edge 970 of the base 910 and the other three 900d', 900e', 900f' at the right hand long edge 971 in a manner so as to have front end portions of the bundles 900a', 900b', 900c', 900d', 900e', 900f' of proto devices extend over the respective edge in oblique forward directions. Near the rear end of the base 910 electrical and, optionally, optical conductors connecting the electrodes and optical fibers of the left hand 900a', 900b', 900c', and right hand 900d', 900e', 900f' bundles are combined in flexible polymer tubes 907, 908. To facilitate insertion into soft tissue the array of proto bundles can be incorporated in a shell of a water soluble material (not shown).

After insertion into soft tissue, the array 950 of bundles 900a', 900b', 900c', 900d', 900e', 900f' of proto devices of the invention is transformed to a corresponding array of bundle of devices of the invention (not shown) by dissolution, degradation or swelling of their stiffening elements.

Example 14

Second Embodiment of an Array of Bundles of Proto Devices of the Invention

Figure 12:
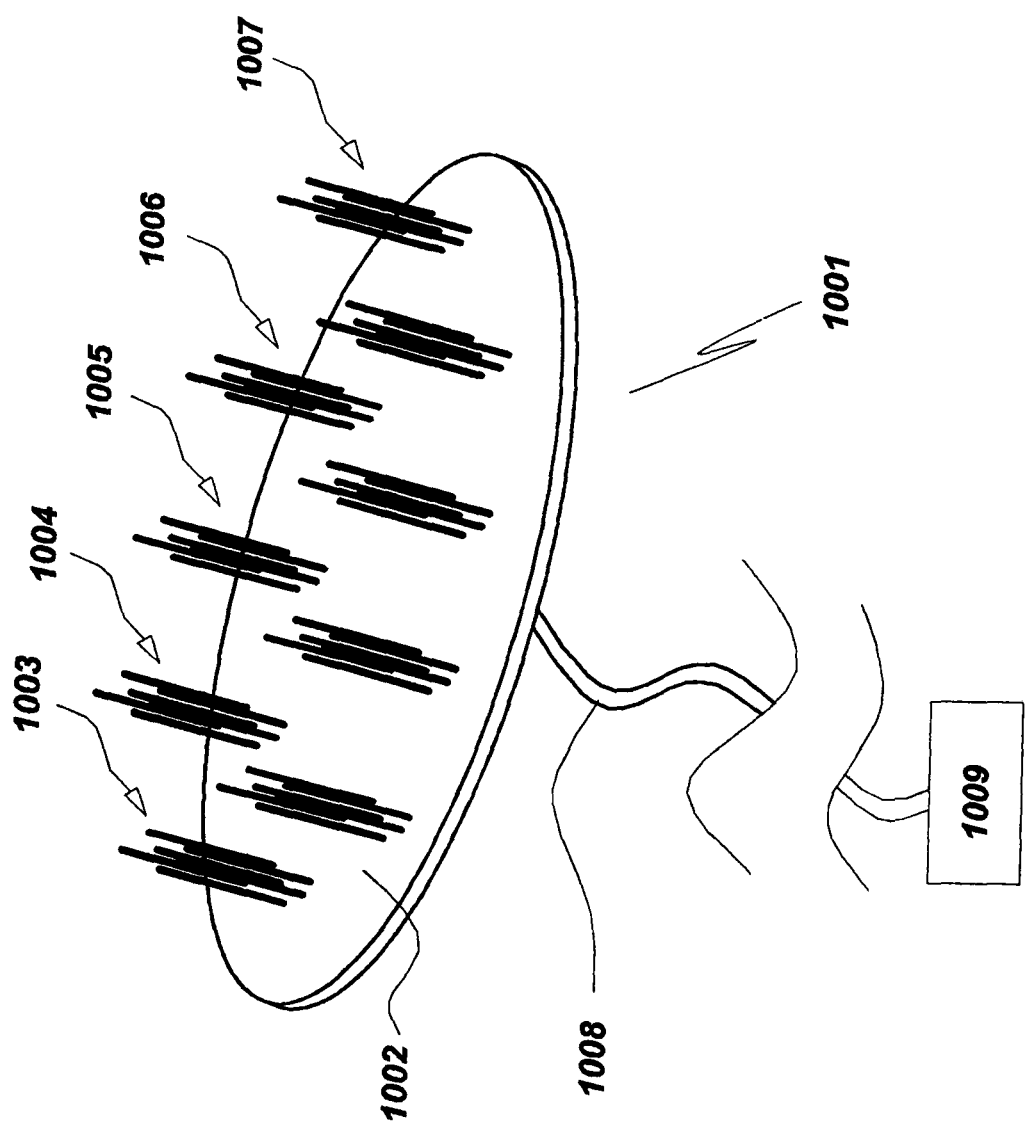
FIG. 12 an array comprising nine bundles, each bundle comprising five proto devices of the invention, in an angular side view.

The array 1001 of FIG. 12 comprises a thin circular flat support of polyurethane 1002 from one (top) face of which nine bundles of proto devices of the invention 1003, 1004, 1005, 1006, 1007, etc. of the invention extend perpendicularly so as to be disposed in parallel in respect of each other. Each bundle comprises five proto devices of the invention.

The proto devices of the bundles 1003, 1004, 1005, 1006, 1007, etc. penetrate the support 1002 and extend for a short distance from its other (bottom) face. They are bundled in a flexible tube 1008 and optically and electrically connected with a control unit 1009. The control unit 1009 allows a person to activate optical fibers and electrodes of selected bundle(s) and even selected optical fibers and electrodes of one bundle, as well as to receive optical and electrical signals emitted from soft tissue for transmission to the control unit. The control unit 1009 also allows a person transmit radiation of different kind through selected optical fibers of the bundles. Various energizing and radiation patterns can thus be realized as well as electrical signal and radiation patterns emanating from soft tissue received and detected.

Example 15

Eleventh Embodiment of the Proto Device of the Invention

Figure 13:
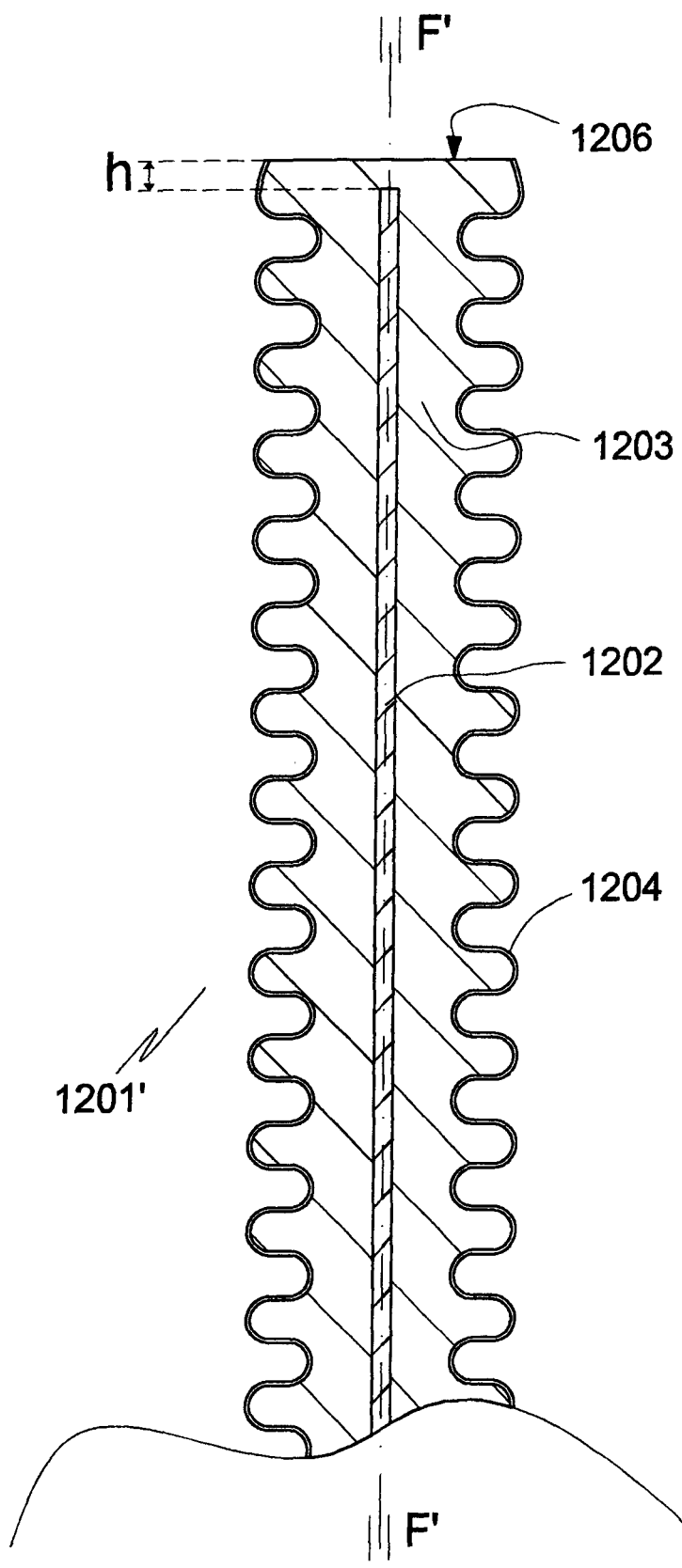
FIG. 13 a distal portion of an eleventh embodiment of the proto device of the invention, in an axial section.

In FIG. 13 is shown an axial section F'-F' of a distal terminal portion of a tenth embodiment 1201' of the proto device of the invention. Reference number 1202 identifies a combination of optical fiber and electrode, which is withdrawn in a proximal direction by a distance h from the distal face 1206 a bellows-shaped stiffening element 1203 of corresponding geometry on which a correspondingly shaped flexible polymer coat 1204 is disposed. On dissolution of the water soluble stiffening element 1203 by tissue fluid contacting the stiffening element 1203 at its flat distal face 1206 a corresponding device of the invention is formed. The coat 1204 of device of the invention thus formed is extendible in a proximal/distal direction, thereby is designed to adapt to movements of different portion of the tissue into which the device is inserted, and to be anchored in the tissue.

Example 16

Twelfth Embodiment of the Proto Device of the Invention

Figures 14A, 14B:
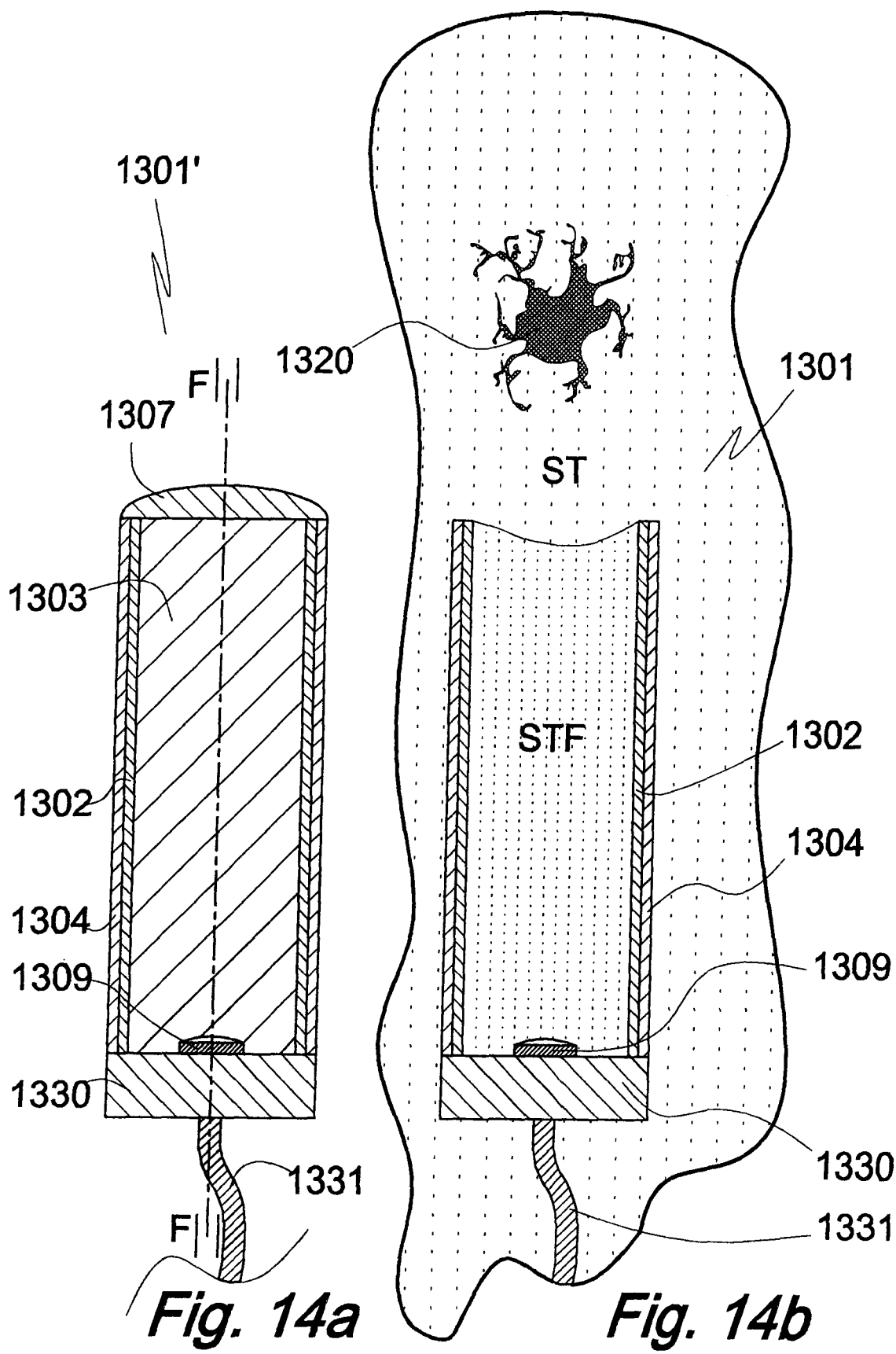
FIG. 14a an eleventh embodiment of a proto device of the invention, in an axial section.
FIG. 14b a twelfth embodiment of the device of the invention corresponding to the proto device of FIG. 14a, in the same view.

The rotationally symmetric (central axis F-F) twelfth embodiment of the proto device 1301' of the invention illustrated in FIG. 14*a* comprises an LED 1309 as a light source and a cylindrical layer 1302 of gold or platinum on the inner face of a cylindrical flexible polymer coat 1302. A cap 1307 of a water soluble material is attached to the distal face of the coat 1304, the proximal end of which is attached to a circular base 1330. The coat 1304/gold layer 1308, the cap 1307 and the base 1330 define a cylindrical space occupied by a stiffening element 1303 of a water soluble mixture of glucose and albumin or gelatin selected from natural gelatin and gelatin cross linked by heat or chemically. The LED 1309 and the electrode layer 1302 are electrically connected with a control unit (not shown) via a multiple lead 1331.

Upon insertion of the proto device 1301' into soft tissue ST the stiffening element is contacted by aqueous soft tissue fluid STF at its distal face and dissolved. A device of the invention 1301 is thereby formed, FIG. 14*b*. Over time the solution of glucose and albumin in the void formerly occupied by the stiffening element 1303 is substituted by pure soft tissue fluid STF or, if the stiffening element is swellable like gelatin the void becomes filled with a translucent gel. By energizing the LED a neuron 1320 disposed distally of the device 1301 is irradiated. By detecting light fluorescent light emitted from the neuron 1320 is position relative to the device 1301 can be determined, allowing the device to be displaced in a desired direction in respect of the neuron to dispose it optimally for optical and/or electric interaction with the neuron 1320.

Example 17

Thirteenth Embodiment of the Proto Device of the Invention

Figure 15:
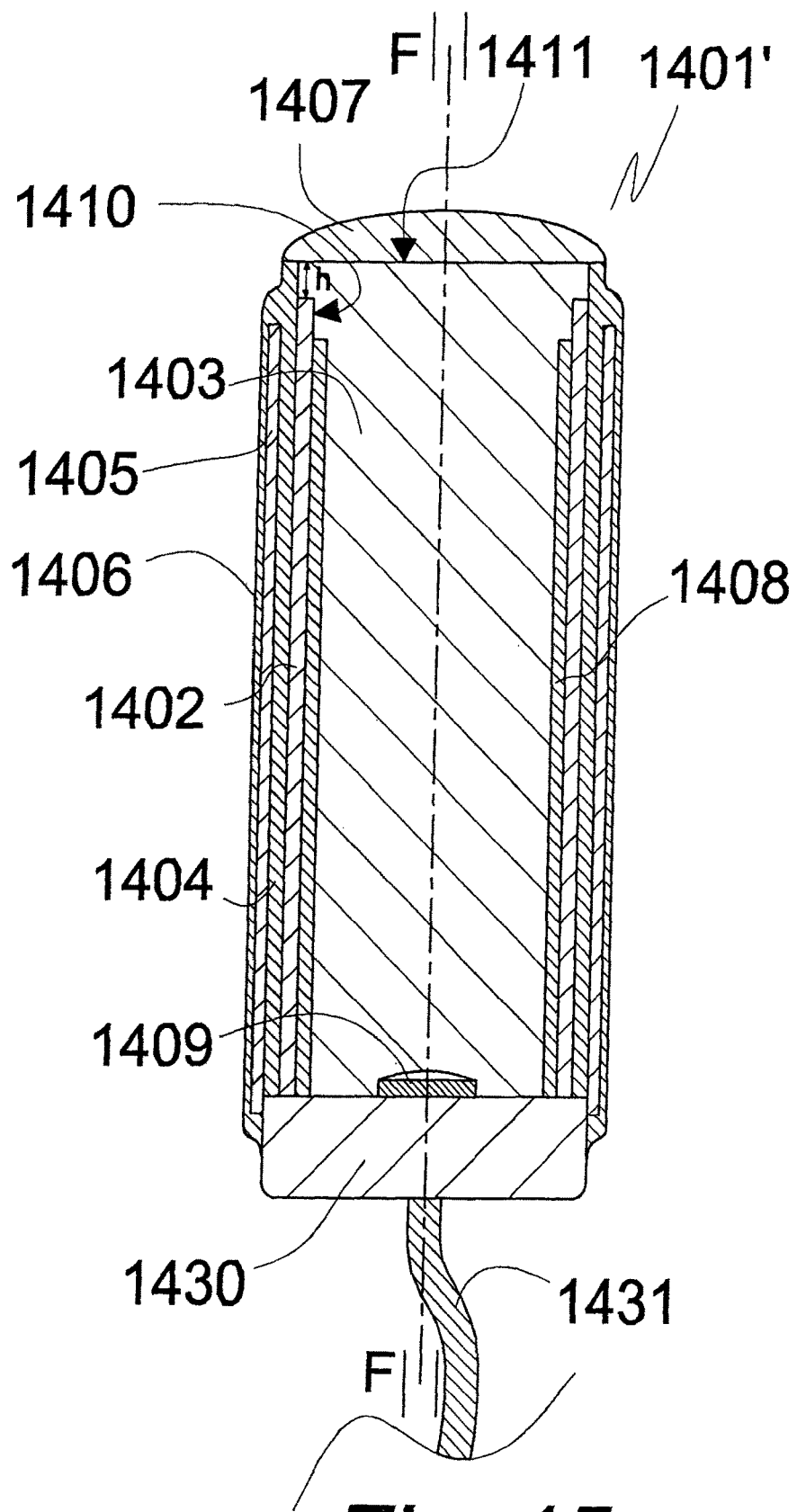
' and FIGS. 15, 16 is comprised by all embodiments of the prestage device, the proto device and the device of the invention.

The twelfth embodiment 1401' of the proto device of the invention shown in FIG. 15 corresponds to the eleventh embodiment 1301' of FIG. 14*a* except for the electrode being insulated except at its distal terminal portion and by a shielding metallic layer 1405 being disposed on the outer face of the flexible polymer coat 1404. On its outer face the shielding layer 1405 is covered by a coat 1406 of same material as the coat 1404 so as to be fully insulated. The layer 1404 shielding the electrode 1402 is kept on earth potential to protect the electrode 1402 from being disturbed by external electrical fields. The electrode 1402 is insulated by a lacquer 1408 at its inner face except for a small portion at 1410 extending from its distal end. To avoid or at least delay contact with soft tissue the electrode 1402 is withdrawn in a proximal direction by a distance h from the distal faces 1411 of the stiffening element 1403 and the flexible polymer coat 1404. The electrode layer 1402 and the shielding layer 1405 as well as the flexible polymer layers 1404, 1406 are attached to the base 1430 and electrically connected with the multiple lead 1431 via the base 1430. The elements identified by reference numbers 1407 and 1409 correspond to elements 1307 and 1309, respectively, of the embodiment of FIG. 14*a*.

Example 18

Coating an Metallic or Polymer Element with Water Soluble Material

From the combination of optical fiber and electrical conductor or light source grease and oil are removed by dipping the combination into diethyl ether for 10 seconds, removing it and drying. A sugar coating of about 30 µm thickness is applied to the combination in the following manner. Sucrose (100 g) is dissolved in 50 ml water. The solution is boiled for about 5 min until it appears clear. The solution is allowed to cool to 80° C. The combination held at its rear end by a pair of stainless steel pincers is dipped fully into the solution. It is removed from the solution by withdrawing it vertically with a speed of 6 mm/s. The sucrose coated combination is dried overnight so as to form a dry sucrose coat on the body of about 40 µm thickness. The thickness of the coat can be selected by varying the speed of withdrawal and or by multiple dipping. Lowering the speed renders a thinner coat.

Example 19

Manufacture of a Prestage of Device the Invention by Coating the Dry Sucrose Element of Example 14 with Parylene C A coat of Parylene C of about 4 µm thickness is applied by a state-of-the-art vacuum coating process (http://www.scscookson.com/parylene/properties.cfm) in which diparaxylylene is vaporized and then pyrolized to paraxylylene, which is adduced under high vacuum to a deposition chamber kept at about room temperature and there deposited on the sucrose coated element of Example 17. The twice coated device thus obtained corresponds to a prestage device of the invention.

Example 20

Manufacture of a Proto Device of the Invention from the Prestage Device of Example 19

The prestage device of Example 18 is dipped with its front end foremost into molten high melting paraffin (m.p. of about 40° C.) in a short 3 mm diameter polypropylene cylinder. After cooling to room temperature, the paraffin block containing the prestage device is put on a polypropylene support and cut radially with a razor blade so as to sever its tip. After removing most of the paraffin by melting the block and withdrawing the proto device thus formed the latter is rinsed several times with pentane and dried. The recorded impedance of the insulated electrode body prior to cutting is >10 megohm, measured with the electrode body immersed into saline. The recorded impedance after cutting the tip and immersion of the proto device into saline for 2-3 h is <50 kohm. Alternatively, the prestage device of Example 15 is fixed under a microscope and portions of the Parylene C coat near the front end are removed by scraping the coat with a micro file made by coating a thin steel wire (0.1 mm diameter) with titanium oxide powder (grain of about 10 µm) by means of cyanoacrylate pre-polymer dissolved in diethyl ether, into which the wire is dipped immediately prior to the application of the powder.

Dimensions of the proto device can vary within a broad range: diameters of up to 100 µm or more are useful. A preferred diameter is from 5-30 µm. The length of the proto device can be adapted to its desired location after insertion.

Example 21

Fourteenth Embodiment of the Proto Device of the Invention

Figure 16:
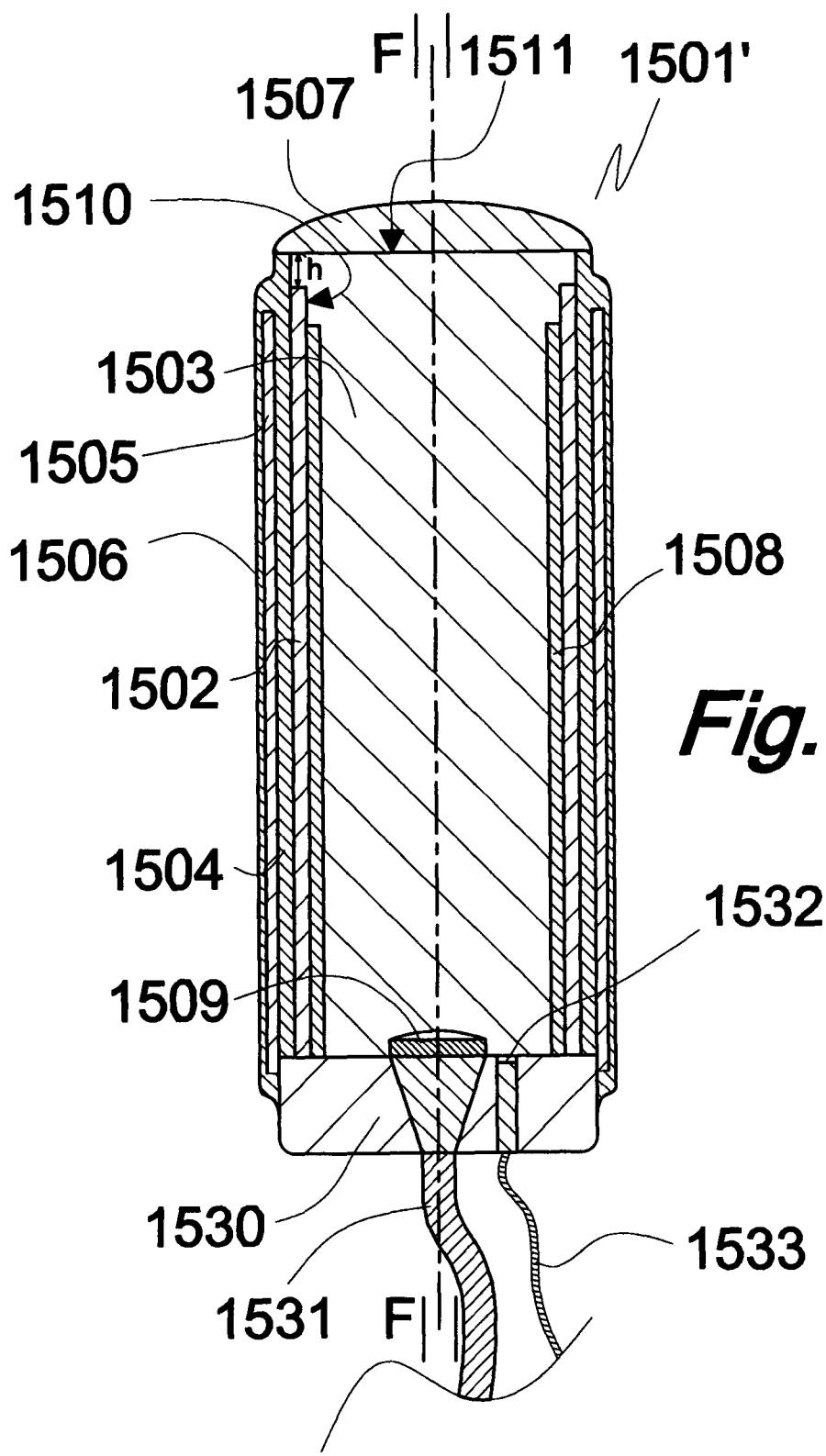

The fourteenth embodiment 1501' of the proto device of the invention shown in FIG. 16 differs from the thirteenth embodiment 1401' by comprising, in addition to a light source 1509 mounted in basis 1530, a light sensor 1532, in particular one for fluorescent light, also mounted in basis 1530. The radiation sensor 1532 is electrically connected by a flexible, electrically conducting wire 1533 with a recording unit (not shown) comprising a microprocessor, a memory and a data output means such as a printer. The other features 15XX of the proto device 1501' correspond to respective features 14XX of the proto device 1401' of the thirteenth embodiment.

Example 22

Fifteenth Embodiment of the Proto Device of the Invention and of a Corresponding Device of the Invention Formed from the Proto Device Upon Implantation into Soft Tissue The fifteenth embodiment 1601' of the proto device of the invention shown in FIGS. 17, 29 comprises a stiffening element 1603, which is degradable or soluble in aqueous body fluid. The stiffening element 1603 is mounted on a rigid cylindrical base 1613 of polymer material such as highly cross-linked polyurethane. An LED light source 1609 is mounted on the distal face of the base 1613 and is energized by means of an insulated flexible conductor 1614 connected to a power source. The stiffening element 1603 is of substantially cylindrical form a rotationally symmetric in respect of its longitudinal axis F-F. The stiffening element 1613 and the base 1603 have about the same diameter. The stiffening element 1603 is covered by consecutive layers of electrically insulating flexible polymer 1608, an electrically conducting flexible electrode layer 1604, and a flexible coat layer 1602. The flexible electrode layer 1604 has been attached to the insulating polymer layer 1608 and, to a narrow zone distal zone of the stiffening element 1603 not covered by the insolating polymer layer 1608 by a suitable method such as metal ion sputtering. Metals of high conductivity like gold and copper, are preferred for this purpose. The polymer layers 1608 and 1602 have been attached by dipping the proto device under formation in solutions of the respective polymer in an organic solvent of low polarity in which the stiffening element 1603 material is not soluble. The distal face 1611 of the stiffening element is then covered with a rounded cap 1610 of a material, which is readily soluble in aqueous body fluid. The cap 1610 is provided to facilitate insertion of the device into soft tissue. To avoid or at least make contact upon implantation of the electrode with surrounding soft tissue more difficult the electrode layer 1604 is slightly withdrawn from the distal rim of the flexible polymer coat as indicated by "h" in FIG. 17. A distal terminal portion of the electrode layer 1604 is not covered by the insulating inner flexible polymer layer 1608 to provide for electrical contact with body fluid. In addition to the distal axial opening 1615 are provided three distal radial openings 1605, 1606, 1607 of circular form with their centers disposed in the same radial plane B-B. The radial openings are arranged to allow light to emanate in a radial direction to affect or visualize neighboring soft tissue structures. To enhance radial escape of light the inner face of the electrically insulating polymer layer 1608 can be provided with a reflective coat, such as a thin coat of silver or platinum, or by using a polymer with good visible light reflectance properties for layer 1608. The wide beam of visible light emitted by the light source 1609 is directed in a distal direction; a portion of it hits the inner face of the insulting polymer layer or of a reflective coat on that layer. From there it is reflected, in part in the direction of a distal lateral opening 1605, 1606, 1607 through which it escapes. Non-insulated annular portions of the electrode layer 1604 are disposed in the lateral openings, only one 1604* of them being indicated in FIGS. 17 and 18. These two kinds of blank electrode faces can be used in combination. Alternatively, if only one of them is desired to be used, the other can be made inactive by applying a layer of electrically insulating material on it (not shown in the Figures).

Upon implantation into soft tissue the proto device 1601' is transformed into a device 1601 of the invention shown in FIGS. 18, 30 by dissolution or degradation of its stiffening element. "M" designates the inner space of the device 1601 filled with body fluid upon complete dissolution of the stiffening element 1603.

FIG. 31 illustrates a section 1601* of a physically modified wall of the device 1601 of the invention. The modification consists in providing the wall with the form of a meander or bellows form. The wall section 1601* comprises a flexible polymer coat 1604*, an electrode layer 1602*, and an inner insulating polymer layer 1608*. By such modification a device of the invention comprising or consisting of non-resilient wall materials can be made extendible in an axial direction.

Example 23

Sixteenth Embodiment of the Proto Device of the Invention and of a Corresponding Device of the Invention Formed from the Proto Device Upon Implantation into Soft Tissue The proto device 1701' of the invention illustrated in FIG. 19 is shown in an axial view corresponding to the proto device of FIG. 17, from which it differs by substitution of cap 1610 by a portion of its flexible polymer coat 1704. Upon implantation into soft tissue the stiffening element 1703 is dissolved or degraded and substituted by aqueous body fluid. Thereby a corresponding device 1701 of the invention illustrated in FIG. 20 is formed. Reference numbers 17XX in FIGS. 19 and 20 not specifically addressed refer to elements of corresponding kind 16XX illustrated in FIGS. 17 and 18.

Example 24

Seventeenth Embodiment of the Proto Device of the Invention and of a Corresponding Device of the Invention Formed from the Proto Device Upon Implantation into Soft Tissue The proto device 1801' of the invention illustrated in FIG. 21 is shown in an axial view corresponding to the proto device of FIG. 17, from which it differs by provision of an optical sensor 1815 mounted on the distal face of the base 1813. The sensor 1815 is sensitive to visible light. It is particularly suited for monitoring fluorescent radiation of a certain wavelength, and is so selected from a number of commercially available light sensors. It is electrically coupled with a recording unit (not shown) by insulated flexible lead 1816. The recording unit can transform electrical signals from the sensor to numerical data and store these data in a memory. The recording unit is also capable of coordinating tissue irradiation by light source 1809, recording of sensor 1815 data, and electrode 1802 control. Reference numbers 18XX in FIG. 21 not specifically addressed refer to elements of corresponding kind 16XX illustrated in FIGS. 17 and 18. Upon implantation into soft tissue the proto device 1801' is transformed into a device 1801 of the invention by dissolution or degradation of its stiffening element 1803, as shown in FIG. 22.

Example 25

Eighteenth Embodiment of the Proto Device of the Invention and of a Corresponding Device of the Invention Formed from the Proto Device Upon Implantation into Soft Tissue The proto device 1901' of the invention illustrated in FIG. 23 is shown in an axial view corresponding to the proto device of FIG. 17, from which it differs by a reflective inner wall portion 1919 and a distal wall portion 1918 provided with micro openings. The micro openings are provided by laser technique; their function is to provide access of body fluid to the stiffening element 1903 to allow or facilitate its dissolution and the transport of its constituents out of the interior M of the device. The diameter of the micro openings are in the order of a 50 µm or less, more preferred from 5 µm to 30 µm. Reference numbers 19XX in FIG. 23 not specifically addressed refer to elements of corresponding kind 16XX illustrated in FIGS. 17 and 18. Upon implantation into soft tissue the proto device 1901' is transformed into a device 1901 of the invention by dissolution or degradation of its stiffening element 1903, as shown in FIG. 24.

Example 26

Figure 25:
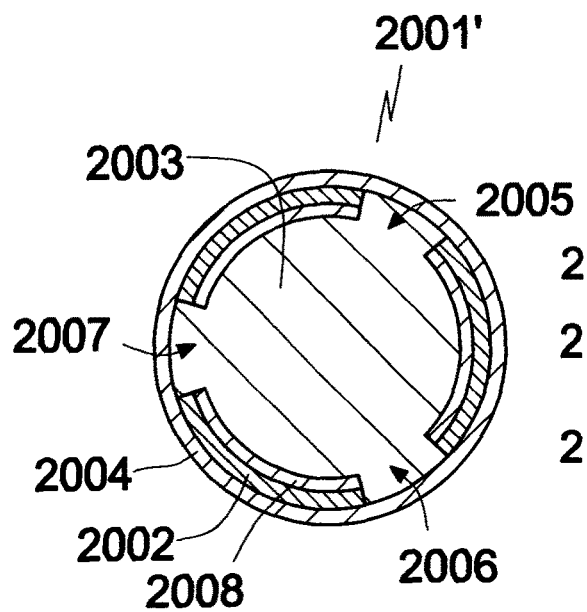
FIG. 25 a nineteenth embodiment of the proto device of the invention in a radial section corresponding to that of the embodiment of FIG. 17 except for having its lateral distal openings covered by a translucent flexible polymer coat.

First Variety of the Proto Device of the Invention Illustrated in FIG. 17 and of a Corresponding Device of the Invention Illustrated in FIG. 18 Formed from the Proto Device Upon Implantation into Soft Tissue The proto device 2001' of the invention illustrated in FIG. 25 is shown in a sectional radial view only, which correspond to the radial view of FIG. 29 of the proto device of FIG. 17 (section B-B). The section B-B dissects the centers of the circular windows 2005, 2006, 2007, which are covered by portions of the flexible polymer coat 2004. The coat 2004 is of a translucent polymer material.

Figure 26:
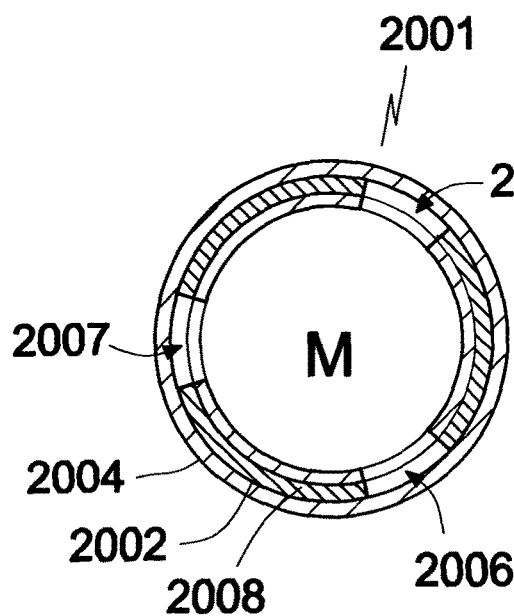
FIG. 26 a device of the invention formed from the proto device of FIG. 25 upon implantation into soft tissue, in a corresponding radial section.

Upon implantation into soft tissue the proto device 2001' is transformed into a device 2001 of the invention by dissolution or degradation of its stiffening element 2003, as shown in FIG. 26. The void filled with body fluid is designated M. Reference numbers 20XX in FIG. 24 not specifically addressed refer to elements of corresponding kind 16XX illustrated in FIG. 17.

Example 27

Figure 27:
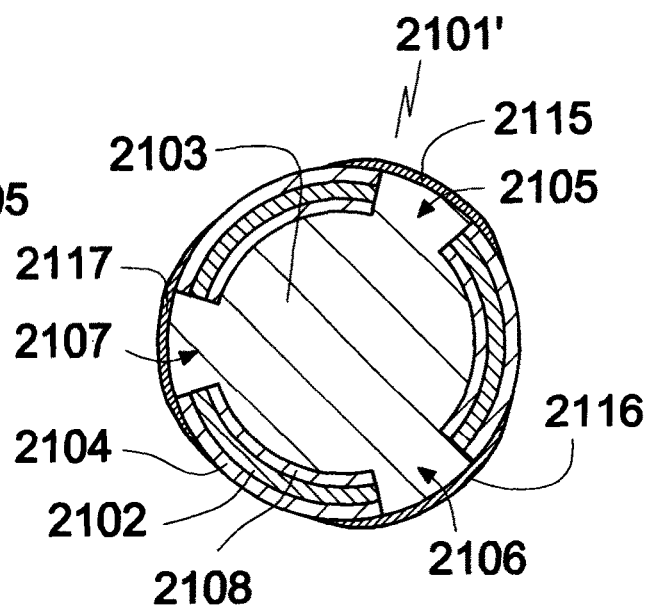
FIG. 27 a twentieth embodiment of the proto device of the invention in a radial section corresponding to that of the embodiment of FIG. 17 except for having its lateral distal openings covered by flexible sheets of translucent polymer material.

Second Variety of the Proto Device of the Invention Illustrated in FIG. 17 and of a Corresponding Device of the Invention Illustrated in FIG. 18 Formed from the Proto Device Upon Implantation into Soft Tissue The proto device 2101' of the invention illustrated in FIG. 27 is shown in a sectional radial view only, which correspond to the radial view of FIG. 29 of the proto device of FIG. 17 (section B-B). The section B-B dissects the centers of the circular windows 2105, 2106, 2107, which are covered sheets of a translucent flexible polymer material 2115, 2116, 2117.

Figure 28:
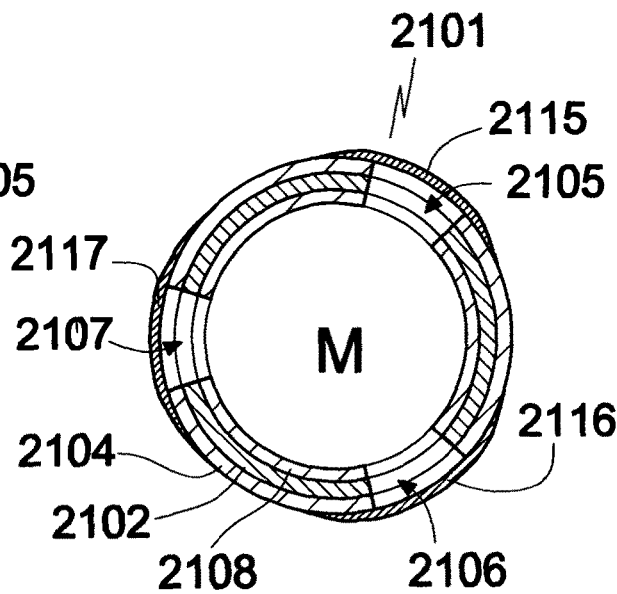
FIG. 28 a device of the invention formed from the proto device of FIG. 27 upon implantation into soft tissue, in a corresponding radial section.

Upon implantation into soft tissue the proto device 2101' is transformed into a device 2101 of the invention by dissolution or degradation of its stiffening element 2103, as shown in FIG. 28. The void filled with body fluid is designated M. Reference numbers 21XX in FIGS. 27, 28 not specifically addressed refer to elements of corresponding kind 16XX illustrated in FIG. 17.

Materials
Electrode.

The electrode is preferably of a noble metal or an alloy of noble metals or comprising noble metals such as gold, silver, platinum, iridium, but other biologically acceptable metals such as stainless steel and tantalum can also be used as well as gold plated copper. Aluminum is a preferred metal for coating an optical glass fiber. Instead of a metal or metal alloy the electrical conductor may consist of or comprise an electrically conducting polymer such as PEDOT. Electrically conducting states of carbon may also be used. Portions of the electrical conductor that are not electrically insulated from tissue fluid upon removal of the first coat may be advantageously provided with surface enlarging elements or structures such as a roughened surface, forests of conducting nanowires, for instance carbon nanowires, or be porous. Surface enlarging structures of this kind will reduce the impedance of the electrical conductor. The electrical connection of the conductor with a control unit can be provided by a metal wire or similar coupled between the rear end of the electrical conductor and the control unit or by the conductor itself, a rear section thereof functioning as an electrical coupling means. In such case the rear section has to be electrically insulated.

Stiffening Element Coat.

The combination of electrode and light source of the invention is embedded in/coated with one or more biocompatible first coat materials, which may be water dissolvable, swellable and/or degradable. If embedded in two or more of such materials they differ in their dissolution rate. Preferred first coat materials are water soluble carbohydrates and proteins as well as mixtures thereof. However, it is also possible to use water insoluble polymer materials swellable in water and/or degradable in body fluid. A suitable stiffening element coat material of which the dissolution time can be controlled is obtained by repeatedly boiling and cooling an aqueous solution of a sugar or a mixture of sugars selected from sucrose, lactose, mannose, maltose and an organic acid selected from citric acid, malic acid, phosphoric acid, tartaric acid. By selecting particular combinations of sugar(s) and organic acid(s) it is possible to obtain materials with different dissolution times. Gelatin may also be used as a first coat material. It is well known that different types of gelatin or gelatin based materials have different dissolution rates. If the first coat of water soluble or swellable material comprises two or more sections disposed along oblong combination of optical fiber/light source and electrode. The selection of a proper combination of gelatins provides a distal first coat section of shorter dissolution time and a proximal first coat section of longer dissolution time. The use of a sugar-based first coat material for the distal first coat section and of a gelatin-based first coat material for the proximal first coat section or vice versa is also possible, as well as the use of gelatin for a distal first coat section and of gum arabic for a first coat proximal section. The selection of further useful combinations of first coat materials, such as various types of natural gums, is within the easy reach of a person skilled in the art. Optionally, first coat materials with substantially longer dissolution times, such as modified collagen, cellulose derivatives, modified starch or other biocompatible materials, such as poly-glycolic acid can also be used.

Optionally a polymer insulating coat of the prestage device, the proto device, the bundle of proto devices and the array or proto devices and bundles of the invention or a further coat of water dissolvable material on the first coat can be covered, completely or in part, by a biocompatible gliding agent to reduce friction during insertion into tissue. Useful gliding agents include glycerol monopalmitate, glycerol dipalmitate, glycerol monostearate, glycerol distearate, palmityl alcohol, stearyl alcohol. A thin coat of gliding agent can be applied by, for instance, spraying with a solution of the agent in ethanol or ethyl acetate.

Flexible Polymer Coat.

In principle, polymer materials of all kinds suitable for electrical insulation can be used. However, the tiny structure of the prestage device of the invention to be produced by polymer coating restricts the number of application methods and useful polymers. While deposition of monomer from the gas phase is preferred, such as for providing a parylene coat, dipping of a prestage device coated with water soluble/swellable/degradable stiffening element material into a polymer or prepolymer solution, withdrawing it from the solution, and evaporating the solvent, optionally allowing a prepolymer to settle, is also useful. The dipping method should take recourse to a polymer solvent that does not interact with the water soluble/swellable/degradable material, in particular a non-polar solvent such as an alkane or alkene or cycloalkane or a non-polar aromatic solvent or a mixture thereof, in particular pentane or hexane but also diethyl ether or dichloromethane. Suitable polymers comprise biocompatible types of polyurethane, polyurethane urea and polyimide. Other useful polymers include silicones of various kind. Further useful polymers include polyethylene terephthalate (PET). The flexible polymer coat of the invention moves with surrounding tissue and does not restrict tissue movement. The thickness of the flexible coat is from a few μm and up to 20 μm or 50 μm or more.

Bundles of Proto Electrodes.

Proto devices of the invention can be bundled in different ways, such as by incorporation of their rear end portions in a base of polymer or other material or by joining their rear end portions with glue. The bundling can be temporary, such as for keepings the devices in a fixed relationship prior to and during insertion into soft tissue, or permanent. A bundle of proto devices comprises a bundling means disposed in a proximal direction from the distal end of the two or more devices comprised by the bundle and aligned in parallel or about in parallel. The bundling means is preferably permanent, that is, is not dissolved or degraded by body fluid but may also be temporary, that is, be dissolved or degraded upon disposition of the bundle in soft tissue. A preferred permanent bundling means is an adhesive, in particular a cold setting polymer adhesive, such as a polyurethane or polyacrylate adhesive. The polymer adhesive is one not dissolvable or degradable by body fluid, except for over very long periods of more than a year or five years the adhesive is applied to the aligned proto devices at proximal portions thereof.

A water dissolvable or degradable adhesive of corresponding properties allows the proto devices to dissociate quickly or slowly upon insertion. A swellable but not water soluble adhesive allows the proto devices inserted into soft tissue and the devices of the invention formed from them to be displaced in a restricted manner while an insoluble and non-swellable adhesive will restrain their movement to bending and, if designed extendable, to changes in length.

Individual proto devices of a bundle may differ in length. For instance, a central proto device of a bundle may be longer than peripheral devices thereof to provide a central bundle point.

Upon insertion into soft tissue, the proto devices of a bundle are transformed to devices of the invention and the bundle of proto devices is thereby transformed to a bundle of devices of the invention.

In this application an array of proto devices or bundles of proto devices forms a proto device pattern comprising numerous proto devices and/or bundles of proto devices bundles of the invention disposed on and attached to at least one face of an electrically non conducting support. Thin supports of a suitable polymer like polypropylene, polyacrylate, polycarbonate and parylene C comprising substantially only two faces are preferred. The supports can be flat but may also be curved. The proto devices and/or bundles of proto devices can be mounted on one or both surfaces of the support. The proto devices and the bundles of proto devices attached to the support can protrude from the support at an angle, in particular an angle of from about 15° to about 75° and even up to about 90°, the angle being one included by the device or bundle of devices and its projection onto the mounting face of the support and/or at an angle of from about 15° to about 75° included by the proto device or proto device bundle long axis and a central long axis of the support. The support may contain pores or be semi-permeable to body fluids, that is, permeable to at least water and inorganic salts.

Upon insertion into soft tissue and contact with aqueous body fluid in the tissue, the proto device, the bundle of proto devices and the array of proto devices or bundles of proto devices are transformed to a corresponding device, a bundle of devices and an array of devices of the invention.

The support of an array of the invention can also be of a material that is soluble or degradable in soft tissue. Useful materials comprise those identified above as useful water soluble/swellable/degradable first coat materials.

If desired an array support can be equipped with a control unit, such as one comprising or consisting of an electronic chip in electric contact with the electrical conductor(s) of individual devices. The control unit can comprise or be in electrical contact with a unit for electric tissue stimulation and/or signal amplifier(s) for recording electrical nerve signals. The array support can also be equipped with a radiation control unit, which comprises radiation emitting means such as one or more LEDs optically coupled with optical fibers of the array. Furthermore the array support can also be equipped with light sensor(s).

What is claimed is:

1. Medical device having a front (distal) end and a rear (proximal) end, comprising:
    a base disposed at the rear end of the medical device, wherein the medical device is configured for insertion into soft tissue;
    a micro electrode and a micro light source, both attached to the base and extending from a distal face of the base in a distal direction;
    a stiffening element coated on the micro electrode and the micro light source, the stiffening element comprising one of:
        a) a material dissolvable or degradable in aqueous body fluid in an amount sufficient to make the stiffening element dissolve or collapse in contact with aqueous body fluid;
        b) a material swellable in aqueous body fluid to form a transparent gel;
    a coat made of a polymer material that is flexible, non-conducting, water insoluble, and non-water-degradable, the polymer coat being on and surrounding the stiffening element, and preventing or at least delaying contact between the micro electrode and soft tissue upon collapse or swelling of the stiffening element, the polymer coat having a distal opening allowing light emitted from the micro light source to leave the medical device upon said dissolving, collapsing, or swelling of the stiffening element.

2. The medical device of claim 1, wherein the micro light source is a member of the group consisting of LED, micro laser, optical fiber receiving light from a source not comprised by the medical device.

3. The medical device of claim 1, wherein the micro electrode comprises a metal or a metal alloy or an electrically conducting polymer.

4. The medical device of claim 2, wherein the micro electrode comprises a rod or a layer on the optical fiber or a layer on the polymer coat surrounding the stiffening element.

5. The medical device of claim 1, wherein the polymer coat is of about cylindrical form.

6. The medical device of claim 1, wherein the micro electrode is electrically insulated except for a portion extending from its distal end in a proximal direction.

7. The medical device of claim 1, wherein the micro electrode is electrically shielded by an electrically conducting layer on an outer face of the polymer coat kept at earth potential.

8. The medical device of claim 1, wherein the stiffening element comprises or consists of a carbohydrate and/or protein material.

9. The medical device of claim 1, comprising a portion extendable in a longitudinal (proximal-distal) direction upon dissolving, collapsing, or swelling of the stiffening element.

10. The medical device of claim 9, wherein said extendable portion comprises a portion of the polymer coat.

11. The medical device of claim 10, wherein said extendable portion is bellows-shaped.

12. The medical device of claim 1, comprising a microprocessor control unit.

13. The medical device of claim 1, wherein the distal end of the micro electrode is withdrawn from the distal opening in a proximal direction.

14. The medical device of claim 2, wherein the distal end of the optical fiber is withdrawn from the distal opening in a proximal direction.

15. The medical device of claim 1, wherein the stiffening element is of about rotationally symmetric form, in particular of about cylindrical form, and comprises two or more cylindrical sections of different composition disposed adjacent to each other in a distal-proximal direction.

16. The medical device of claim 15, wherein at least one of the two or more cylindrical sections comprises a pharmacologically active agent.

17. The medical device of claim 1, wherein the stiffening element comprises two sections of different composition disposed adjacent to each other in a radial direction.

18. The medical device of claim 16, wherein at least one of the two sections comprises a pharmacologically active agent.

19. The medical device of claim 1, comprising a reservoir filled with a solution of a pharmacologically active agent.

20. The medical device of claim 1, comprising at its rear end a means for wireless communication with an external control unit.

21. The medical device of claim 1, wherein the micro electrode, the micro light source and/or the polymer coat is firmly attached to the base.

22. The medical device of claim 1, comprising a radiation sensor.

23. The medical device of claim 22, wherein the radiation sensor is sensitive to visible and/or near infrared light.

24. The medical device of claim 22, wherein the radiation sensor is mounted at the base.

25. The medical device of claim 24, wherein said distal opening is selected from axial distal opening and radial distal opening.

26. The medical device of claim 25, comprising a distal axial opening and one or more distal radial openings.

27. The medical device of claim 25, wherein said distal opening is covered by a sheet of translucent polymer material.

28. The medical device of claim 27, wherein the sheet of translucent material is as flexible or more flexible than the polymer coat.

29. The medical device of claim 25, comprising an inner light-reflecting wall disposed distally of the micro light source.

30. The medical device of claim 25, comprising a distal wall section comprising micro openings.

31. The medical device of claim 30, wherein a diameter of a majority of micro openings is from 5 µm to 50 µm, in particular from 3 µm to 30 µm.

32. The medical device of claim 1, wherein the polymer material is selected from a group consisting of biocompatible polyurethane, polyurethane urea, polyimide, parylene, silicones and polyethylene therephthalate (PET).

33. Therapeutic and/or diagnostic medical device formed in tissue upon insertion of the medical device of claim 1 and dissolving, collapsing, or swelling of said stiffening element, the medical device being configured to provide one or more of: a) emission of light into surrounding soft tissue; b) detection of light emitted from surrounding soft tissue; c) electrical stimulation of surrounding tissue structures; d) detection of electrical signals emitted from surrounding soft tissue.

34. The therapeutic and/or diagnostic medical device of claim 33, further configured for providing optical and/or electrical stimulation to structures of soft tissue such as neurons, for recording electrical signals emanating from said structures, for lesioning said structures, for combined drug delivery, for recording of nerve cell signals and for nerve cell stimulation.

35. A method of disposing the medical device of claim 1 in relation to a selected structure in soft tissue, comprising:
inserting the medical device into soft tissue to make it take up a first position;
maintaining the medical device in the first position until the stiffening element has been dissolved, degraded or swelled to form the transparent gel;
making the micro light source emit light in the direction of the selected structure;
monitoring the position of the selected structure by detecting light reflected from the selected structure;
displacing the medical device in respect of the selected structure.

\* \* \* \* \*